US011957499B2

(12) United States Patent
Yin et al.

(10) Patent No.: US 11,957,499 B2
(45) Date of Patent: Apr. 16, 2024

(54) SYSTEMS, METHODS, DEVICES AND STORAGE MEDIUMS FOR OBTAINING A RADIOGRAPHIC IMAGE

(71) Applicant: SHANGHAI UNITED IMAGING HEALTHCARE CO., LTD., Shanghai (CN)

(72) Inventors: Hui Yin, Shanghai (CN); Yecheng Han, Shanghai (CN)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 353 days.

(21) Appl. No.: 17/452,079

(22) Filed: Oct. 25, 2021

(65) Prior Publication Data

US 2022/0133258 A1   May 5, 2022

Related U.S. Application Data

(63) Continuation of application No. PCT/CN2020/086489, filed on Apr. 23, 2020.

(30) Foreign Application Priority Data

Apr. 23, 2019 (CN) .......................... 201910329714.X
May 30, 2019 (CN) .......................... 201910465642.1
Jul. 30, 2019 (CN) .......................... 201910697400.5

(51) Int. Cl.
  *A61B 6/00* (2006.01)
  *A61B 6/03* (2006.01)
(52) U.S. Cl.
  CPC .............. *A61B 6/542* (2013.01); *A61B 6/032* (2013.01); *A61B 6/4441* (2013.01); *A61B 6/488* (2013.01); *A61B 6/548* (2013.01)

(58) Field of Classification Search
  CPC ....... A61B 6/542; A61B 6/032; A61B 6/4441; A61B 6/488; A61B 6/548; A61B 6/5294; A61B 6/545; A61B 6/544
  See application file for complete search history.

(56) References Cited

U.S. PATENT DOCUMENTS 4,590,603 A   5/1986 Relihan et al.
4,703,496 A   10/1987 Meccariello et al.
(Continued)

FOREIGN PATENT DOCUMENTS

CN   2569512 Y   8/2003
CN   102100562 A   6/2011
(Continued)

OTHER PUBLICATIONS

The Extended European Search Report in European Application No. 20796079.0 dated May 20, 2022, 8 pages.
(Continued)

*Primary Examiner* — Courtney D Thomas
(74) *Attorney, Agent, or Firm* — METIS IP LLC

(57) ABSTRACT

The present disclosure discloses methods and systems for obtaining a radiographic image. The method may include obtaining a control instruction for controlling an imaging device to image a subject; determining, based on information reflecting a user's behavior in using the imaging device, adjustment parameters of a radiation generating device in the imaging device; and based on the control instruction, determining target exposure parameters at least based on a parameter control curve or biological information of the subject, the parameter control curve including a preset first parameter control curve or a second parameter control curve determined based on operation data of the imaging device, and the biological information including at least a weight and an overall content of each component of the subject; and (Continued)

imaging, based on the target exposure parameters, the subject to obtain the radiographic image.

20 Claims, 13 Drawing Sheets

(56) References Cited

U.S. PATENT DOCUMENTS

| | | | |
|---|---|---|---|
| 5,253,281 | A | 10/1993 | Krauss |
| 9,025,855 | B1 | 5/2015 | Christoph et al. |
| 2003/0216665 | A1 | 11/2003 | Masuo et al. |
| 2004/0125921 | A1 | 7/2004 | Allouche et al. |
| 2005/0053195 | A1 | 3/2005 | Groh et al. |
| 2007/0165132 | A1 | 7/2007 | Okasaka |
| 2010/0128063 | A1 | 5/2010 | Huo et al. |
| 2013/0030268 | A1 | 1/2013 | Saito |
| 2013/0156151 | A1* | 6/2013 | Sugaya ............... A61B 6/544 378/16 |
| 2015/0085984 | A1 | 3/2015 | Li et al. |
| 2017/0086772 | A1 | 3/2017 | Vaz et al. |
| 2018/0108128 | A1 | 4/2018 | Schmidt et al. |
| 2018/0353151 | A1 | 12/2018 | Tang |

FOREIGN PATENT DOCUMENTS

| | | |
|---|---|---|
| CN | 102894988 A | 1/2013 |
| CN | 104116518 A | 10/2014 |
| CN | 104146724 A | 11/2014 |
| CN | 104394330 A | 3/2015 |
| CN | 105105776 A | 12/2015 |
| CN | 106210558 A | 12/2016 |
| CN | 106413236 A | 2/2017 |
| CN | 106618622 A | 5/2017 |
| CN | 107374659 A | 11/2017 |
| CN | 107811646 A | 3/2018 |
| CN | 108013887 A | 5/2018 |
| CN | 108056784 A | 5/2018 |
| CN | 108735282 A | 11/2018 |
| CN | 109064990 A | 12/2018 |
| CN | 109276266 A | 1/2019 |
| CN | 109521455 A | 3/2019 |
| CN | 110099502 A | 8/2019 |
| CN | 110192885 A | 9/2019 |
| CN | 110415312 A | 11/2019 |
| EP | 0435528 A2 | 7/1991 |
| EP | 0228648 B1 | 4/1998 |
| JP | 5514450 B2 | 6/2014 |
| WO | 0180739 A1 | 11/2001 |

OTHER PUBLICATIONS

International Search Report in PCT/CN2020/086489 dated Jul. 17, 2020, 8 pages.
Written Opinion in PCT/CN2020/086489 dated Jul. 17, 2020, 10 pages.
First Office Action in Chinese Application No. 201910329714.X dated Jul. 6, 2020, 13 pages.
First Office Action in Chinese Application No. 201910465642.1 dated Mar. 3, 2021, 17 pages.
The Second Office Action in Chinese Application No. 201910697400.5 dated Jul. 2, 2021, 32 pages.
Lu, Heqing et al., An Evaluation on Influence Factors of Radiation Does for the Medical X-ray Computed Tomography, Shanghai Medical Imaging, 2008, 5 pages.
Jiang, Wei, Research on Radiation Properties of Tissue-equivalent Materials in Chengdu Dosimetric Phantoms (CDP), CNKI, 2007, 70 pages.
Zhang, Xinyou et al., Medical Graphics and Image Processing, China Traditional Chinese Medicine Publishing House, 2018, 6 pages.

* cited by examiner

300

```
┌─────────────────────────────────────────────┐   310
│ Obtaining a control instruction for controlling an │ ⌇
│        imaging device to image a subject        │
└─────────────────────────────────────────────┘
                       │
                       ▼
┌─────────────────────────────────────────────┐   320
│ Determining target exposure parameters based on │ ⌇
│             the control instruction             │
└─────────────────────────────────────────────┘
                       │
                       ▼
┌─────────────────────────────────────────────┐   330
│  Imaging the subject based on the target exposure │ ⌇
│                  parameters                     │
└─────────────────────────────────────────────┘
```

Determining an equivalent thickness of the subject based on the candidate exposure parameters and the first target brightness — 810

Determining the target exposure parameters based on the equivalent thickness of the subject and a second target brightness — 820

SYSTEMS, METHODS, DEVICES AND STORAGE MEDIUMS FOR OBTAINING A RADIOGRAPHIC IMAGE

CROSS-REFERENCE TO RELATED APPLICATIONS

This application is a continuation of International Application No. PCT/CN2020/086489, filed on Apr. 23, 2020, which designates the United States of America and claims priority to Chinese Patent Application No 201910329714.X, filed on Apr. 23, 2019, Chinese Patent Application No. 201910465642.1, filed on May 30, 2019, Chinese Patent Application No 201910697400.5, filed on Jul. 30, 2019, the entire contents of each of which are hereby incorporated by reference.

TECHNICAL FIELD

The present disclosure relates to the field of image processing, and in particular, to methods, systems, devices, and storage mediums for obtaining high-quality radiographic images.

BACKGROUND

Nowadays, radiographic devices have been applied in many fields, such as medical diagnosis and treatment, industrial material testing, security inspections, etc. In order to obtain radiographic images that meet the requirements (for example, to meet the requirements of diagnosis or testing, or to meet the requirements of a device operator), appropriate exposure parameters are needed for imaging. Therefore, it is desirable to provide methods for obtaining a radiographic image based on appropriate exposure parameters.

SUMMARY

According to an aspect of the present disclosure, a method for obtaining a radiographic image is provided. The method may include at least one operation of operations including: obtaining a control instruction for controlling an imaging device to image a subject; determining, based on the control instruction, target exposure parameters, the target exposure parameters being determined based on at least a parameter control curve, or biological information of the subject; the parameter control curve including a preset first parameter control curve or a second parameter control curve determined based on operation data of the imaging device, and the biological information including at least a weight and an overall content of each component of the subject; and imaging, based on the target exposure parameters, the subject to obtain the radiographic image.

According to an aspect of the present disclosure, a system for obtaining a radiographic image is provided. The system may include at least one processor and at least one storage. The storage may be configured to store instructions, and when executing the instructions, the processor may be configured to direct the system to perform at least one operation of operations including: obtaining a control instruction for controlling an imaging device to image a subject; determining, based on the control instruction, target exposure parameters, the target exposure parameters being determined based on at least a parameter control curve, or biological information of the subject; the parameter control curve including a preset first parameter control curve or a second parameter control curve determined based on operation data of the imaging device, and the biological information including at least a weight and an overall content of each component of the subject; and imaging, based on the target exposure parameters, the subject to obtain the radiographic image.

According to an aspect of the present disclosure, a method for obtaining a radiographic image is provided. The method may include at least one operation of operations including: receiving a control instruction; pre-imaging a subject by delivering radiation to the subject based on the control instruction to obtain candidate exposure parameters; and imaging the subject again by delivering radiation to the again according to the candidate exposure parameters to obtain a radiographic image of the subject.

In some embodiments, the candidate exposure parameters may be pre-imaging exposure parameters when a difference between a brightness of a pre-imaging image and a preset first target brightness satisfies a preset condition.

In some embodiments, the obtaining candidate exposure parameters may include at least one operation of operations including: obtaining pre-imaging exposure parameters, and a brightness of at least one frame of a pre-imaging image; comparing the brightness to a preset first target brightness; and updating, based on the comparison result and an ABS curve, the pre-imaging exposure parameters so that a difference between a brightness of a pre-imaging image and the first target brightness satisfies a preset condition, and using the updated pre-imaging exposure parameters as the candidate exposure parameters.

In some embodiments, the performing imaging on the subject delivering radiation again according to the candidate exposure parameters to obtain a radiographic image of the subject may include at least one operation of operations including: generating, based on candidate exposure parameters, target exposure parameters; and performing, based on the target exposure parameters, imaging on the subject delivering radiation again to obtain a radiographic image of the subject.

In some embodiments, the candidate exposure parameters and the target exposure parameters comprise a tube voltage, a tube current, and an irradiation duration. The determining target exposure parameters based on the candidate exposure parameters may include at least one operation of operations including: adjusting at least one of the tube voltage, the tube current, or the irradiation duration included in the candidate exposure parameters to obtain the target exposure parameters.

In some embodiments, the determining target exposure parameters based on candidate exposure parameters may include at least one operation of operations including: determining, based on the candidate exposure parameters and the first target brightness, an equivalent thickness of the subject; and determining, based on the equivalent thickness of the subject and a second target brightness, the target exposure parameters.

In some embodiments, the determining an equivalent thickness of the subject may include at least one operation of operations including: determining, based on the candidate exposure parameters, the first target brightness, and a brightness-thickness-parameter model, the equivalent thickness of the subject; the brightness-thickness-parameter model including at least a correlation between an image brightness, a subject thickness, and exposure parameters.

In some embodiments, determining the brightness-thickness-parameter model may include at least one operation of operations including: obtaining exposure parameters corresponding to image brightness of a plurality of test targets with different thicknesses when the image brightness reaches a plurality of different brightness; determining a plurality of fitting functions between a plurality of test target thicknesses and corresponding exposure parameters at different brightness and using the fitting function as the brightness-thickness-parameter model; or training an initial model to obtain a trained brightness-thickness-parameter model based on a plurality of test target thicknesses, exposure parameters, and the brightness of the corresponding image. The initial model is a statistical model or a machine learning model.

In some embodiments, the brightness-thickness-parameter model may include a tube voltage and a tube current. A relationship between the tube voltage and the tube current may obey an ABS curve.

In some embodiments, the method may be applied to a C-arm radiographic system.

In some embodiments, the C-arm radiographic system may include a mobile C-arm or a digital subtraction angiography (DSA) device.

In some embodiments, the control instruction may be from an exposure hand brake.

According to another aspect of the present disclosure, a system for obtaining a radiographic image is provided. The system may include an obtaining module, a parameter determination module, and an image obtaining module. The parameter receiving module may be configured to receive a control instruction. The parameter determination module may be configured to pre-image a subject by delivering radiation to the subject to obtain candidate exposure parameters based on the control instruction. The image acquisition module may be configured to perform imaging on the subject delivering radiation again according to the candidate exposure parameters under the control instruction to obtain a radiographic image of the subject.

In some embodiments, the candidate exposure parameters may be pre-imaging exposure parameters when a difference between a brightness of a pre-imaging image and a preset first target brightness satisfies a preset condition.

In some embodiments, in order to obtain candidate exposure parameters, the parameter obtaining module may be further configured to perform at least one operation of operations including: obtaining pre-imaging exposure parameters, and a brightness of at least one frame of a pre-imaging image; comparing the brightness to a preset first target brightness; and updating, based on the comparison result and an ABS curve, the pre-imaging exposure parameters so that a difference between a brightness of a pre-imaging image and the first target brightness satisfies a preset condition, and using the updated pre-imaging exposure parameters as the candidate exposure parameters.

In some embodiments, in order to perform imaging on the subject delivering radiation again according to the candidate exposure parameters to obtain a radiographic image of the subject, the parameter determination module may be further configured to generate target exposure parameters based on candidate exposure parameters. The image acquisition module may be further configured to perform imaging on the subject delivering radiation again based on the target exposure parameters to obtain a radiographic image of the subject.

In some embodiments, the candidate exposure parameters and the target exposure parameters comprise a tube voltage, a tube current, and an irradiation duration. In order to determine target exposure parameters based on candidate exposure parameters, the parameter determination module may be further configured to perform at least one operation of operations including: adjusting at least one of the tube voltage, the tube current, or the irradiation duration included in the candidate exposure parameters to obtain the target exposure parameters.

In some embodiments, in order to determine target exposure parameters, the parameter determination module may be further configured to perform at least one operation of operations including: determining, based on the candidate exposure parameters and the first target brightness, an equivalent thickness of the subject; and determining, based on the equivalent thickness of the subject and a second target brightness, the target exposure parameters.

In some embodiments, in order to determine an equivalent thickness of the subject, the parameter determination module may be further configured to perform at least one operation of operations including: determining, based on the candidate exposure parameters, the first target brightness, and a brightness-thickness-parameter model, the equivalent thickness of the subject. The brightness-thickness-parameter model may include at least a correlation between an image brightness, a subject thickness, and exposure parameters.

In some embodiments, the system may further include a model determination module configured to perform at least one operation of operations including: obtaining exposure parameters corresponding to image brightness of a plurality of test targets with different thicknesses when the image brightness reaches a plurality of different brightness; determining a plurality of fitting functions between a plurality of test target thicknesses and corresponding exposure parameters at different brightness and using the fitting function as the brightness-thickness-parameter model; or training an initial model to obtain a trained brightness-thickness-parameter model based on a plurality of test target thicknesses, exposure parameters, and the brightness of the corresponding image. The initial model is a statistical model or a machine learning model.

In some embodiments, the brightness-thickness-parameter model may include a tube voltage and a tube current. A relationship between the tube voltage and the tube current may obey an ABS curve.

In some embodiments, the method may be applied to a C-arm radiographic system.

In some embodiments, the C-arm radiographic system may include a mobile C-arm or a digital subtraction angiography (DSA) device.

In some embodiments, the control instruction may be from an exposure hand brake.

According to an aspect of the present disclosure, a device for obtaining a radiographic image is provided. The device may include a processor and a storage. The storage may be configured to store instructions, when executing the instructions, the processor may be configured to direct the device to perform any one of the operations to obtain a radiographic image as described above.

According to an aspect of the present disclosure, a computer-readable storage medium may be provided. The storage media may be configured to store computer instructions, and when reading the computer instructions in the storage medium, a computer may perform any one of the operations to obtain the radiographic images described above.

One of the embodiments of the present disclosure provides a method for adaptively controlling an imaging device. The method may include obtaining information reflecting a user's behavior in using an imaging device; determining, according to the information reflecting a user's behavior in using the imaging device, adjustment parameters of a radiation generating device in the imaging device; and generating or correcting, based on the adjustment parameters, a parameter control curve of the radiation generating device, the parameter control curve reflecting a mapping relationship between at least two adjustment parameters of the radiation generating device, and the at least two adjustment parameters including at least two of a tube voltage, a tube current, a pulse effective time, or a product of a tube current and a pulse effective time.

In some embodiments, the information reflecting a user's behavior in using the imaging device comprises at least one of a parameter record of the imaging device manually adjusted by a user, a user's satisfactory degree of an image output by the imaging device, a part to be imaged by a user using the imaging device, or a positioning area of a region of interest in an image output by the imaging device.

In some embodiments, the determining adjustment parameters of a radiation generating device in the imaging device according to the information reflecting a user's behavior in using the imaging device may include using at least one parameter of the parameter record of the imaging device manually adjusted by a user as an adjustment parameter of the radiation generating device in the imaging device.

In some embodiments, the determining adjustment parameters of a radiation generating device in the imaging device according to the information reflecting a user's behavior in using the imaging device may include determining parameters of an imaging device corresponding to an output image as adjustment parameters of the radiation generating device in the imaging device when a user's satisfactory degree of the image output by the imaging device is greater than a preset threshold.

In some embodiments, the determining adjustment parameters of a radiation generating device in the imaging device according to the information reflecting a user's behavior in using the imaging device may include extracting a characteristic value of an output image when a user's satisfactory degree of the image output by the imaging device is greater than a preset threshold; and determining, based on the characteristic value of the output image, adjustment parameters of the radiation generating device in the imaging device.

In some embodiments, the characteristic value of the output image may include at least one of a signal-to-noise ratio, a resolution, a contrast, or an edge sharpness of an image.

In some embodiments, when any one of the following conditions is satisfied, it is determined that the user's satisfactory degree of an image output by an imaging device is greater than a preset threshold. A time that the user uses the imaging device under the quality of the output image is greater than a set time threshold. A count of times the user uses the imaging device under the quality of the output image is greater than a set count threshold. The user saves or confirms under the output image.

In some embodiments, the generating or correcting, based on the adjustment parameters, a second parameter control curve of the radiation generating device may include generating or correcting, according to a part to be imaged by a user using the imaging device, a second parameter control curve of the radiation generating device with respect to the part based on the adjustment parameters.

In some embodiments, the generating or correcting, based on the adjustment parameters, a second parameter control curve of the radiation generating device may include generating or correcting, according to a positioning area of a region of interest in an image output by the imaging device, a second parameter control curve when the radiation generating device irradiates according to the positioning area based on the adjustment parameters.

In some embodiments, the generating or correcting, based on the adjustment parameters, a second parameter control curve of the radiation generating device may include determining, according to the adjustment parameters, at least a part of the second parameter control curve by using an interpolation method or a regression method.

One of the embodiments of the present disclosure provides a system for adaptively controlling an imaging device. The system may include an obtaining module, an adjustment parameter determination module, and a parameter control curve determination module. The obtaining module may be configured to obtain information reflecting a user's behavior in using an imaging device. The adjustment parameter determination module may be configured to determine, according to the information reflecting a user's behavior in using the imaging device, adjustment parameters of a radiation generating device in the imaging device. The parameter control curve determination module may be configured to generate or correct, based on the adjustment parameters, a parameter control curve of the radiation generating device. The parameter control curve may reflect a mapping relationship between at least two adjustment parameters of the radiation generating device, and the at least two adjustment parameters may include at least two of a tube voltage, a tube current, a pulse effective time, or a product of a tube current and a pulse effective time.

One of the embodiments of the present disclosure provides a device for adaptively controlling an imaging device. The device may include at least one processor and at least one storage device. The storage device may be configured to store instructions, and when executing the instructions, the at least one processor may be configured to perform operations including: obtaining information reflecting a users behavior in using an imaging device; determining, according to the information reflecting a users behavior in using the imaging device, adjustment parameters of a radiation generating device in the imaging device; and generating or correcting, based on the adjustment parameters, a parameter control curve of the radiation generating device, the parameter control curve reflecting a mapping relationship between at least two adjustment parameters of the radiation generating device, and the at least two adjustment parameters including at least two of a tube voltage, a tube current, a pulse effective time, or a product of a tube current and a pulse effective time.

One of the embodiments of the present disclosure provides a computer-readable storage medium. The storage medium may be configured to store computer instructions. When reading the computer instructions stored in storage medium, the computer may perform the method for adaptively controlling an imaging device according to any embodiment of the present disclosure.

One of the embodiments of the present disclosure provides a method for determining a dose based on radiography. The method may include at least one operation of operations including: obtaining a weight and an overall content of each component of a subject; determining, according to the scanning part, the weight, and the overall content of each component of the subject, each local component contained in the scanning part, and the local content of each component of the local components; determining, according to component attenuation information of each of the local components to a preset ray spectrum and the component local content of the corresponding local component, total attenuation information corresponding to the scanning part;

and determining, according to the total attenuation information, a dose corresponding to the scanning part.

In some embodiments, obtaining an overall content of each component of the subject may include obtaining, based on a bio-impedance analysis, an overall content of each component of the subject.

In some embodiments, determining, according to the scanning part, the weight, and the overall content of each component of the subject, each local component contained in the scanning part, and the local content of each component of the local components may include determining, according to the scanning part and a reference component contained in each predetermined part, each component of the local components contained in the scanning part; determining, according to the weight and a predetermined reference content ratio of each component of the local components, a target content ratio of each component of the local components; and determining, according to each ratio of the target content ratios and the overall content of each component, the local content of each component of the local components.

In some embodiments, the method may further include obtaining body shape information of the subject. The body shape information may include a height, a body width, and a body thickness.

In some embodiments, determining, according to the scanning part, the weight, and the overall content of each component of the subject, each local component contained in the scanning part, and the local content of each component of the local components may include determining, according to the scanning part and a reference component contained in each predetermined part, each component of the local components contained in the scanning part; determining, according to the weight, the body shape information, and a predetermined reference content ratio of each component of the local components, a target content ratio of each component of the local components; and determining, according to each ratio of the target content ratios and the overall content of each component, the local content of each component of the local components.

In some embodiments, determining, according to component attenuation information of each of the local components to a preset ray spectrum and the component local content of the corresponding local component, total attenuation information corresponding to the scanning part may include determining, according to the body thickness, the body width, and component attenuation information of each of the local components to a preset ray spectrum and the component local content of the corresponding local component, total attenuation information corresponding to the scanning part.

In some embodiments, the component attenuation information is an attenuation coefficient of the local component under the preset radiation spectrum.

According to an aspect of the present disclosure, a device for determining a dose based on radiography is provided. The device may include a component overall content obtaining module, a component local content determination module, a total attenuation information determination module, and a dose determination module. The component overall content obtaining module may be configured to obtain a weight and an overall content of each component of the subject. The component local content determination module may be configured to determine, according to the scanning part, the weight, and the overall content of each component of the subject, each local component contained in the scanning part, and the local content of each component of the local components. The total attenuation information determination module may be configured to determine according to component attenuation information of each of the local components to a preset ray spectrum and the component local content of the corresponding local component, total attenuation information corresponding to the scanning part. The dose determination module may be configured to determine, according to the total attenuation information, a dose corresponding to the scanning part.

According to an aspect of the present disclosure, an electronic device is provided. The electronic device may include one or more processors, and a storage device configured to store one or more programs. When the one or more programs are executed by the one or more processors, the one or more processors may implement a method for determining a dose based on radiography as described above.

According to an aspect of the present disclosure, a computer-readable storage medium is provided. The computer-readable storage medium may be configured to store a computer program. When executed by a processor, the computer program may implement a method for determining a dose based on radiography as described above.

BRIEF DESCRIPTION OF THE DRAWINGS

The present disclosure is further illustrated in terms of exemplary embodiments. These exemplary embodiments are described in detail with reference to the drawings. These embodiments are non-limiting exemplary embodiments, in which like reference numerals represent similar structures throughout the several views of the drawings, and wherein:

FIG. 3 is a flowchart illustrating an exemplary process for obtaining a radiographic image according to some embodiments of the present disclosure;

DETAILED DESCRIPTION

Figure 1:
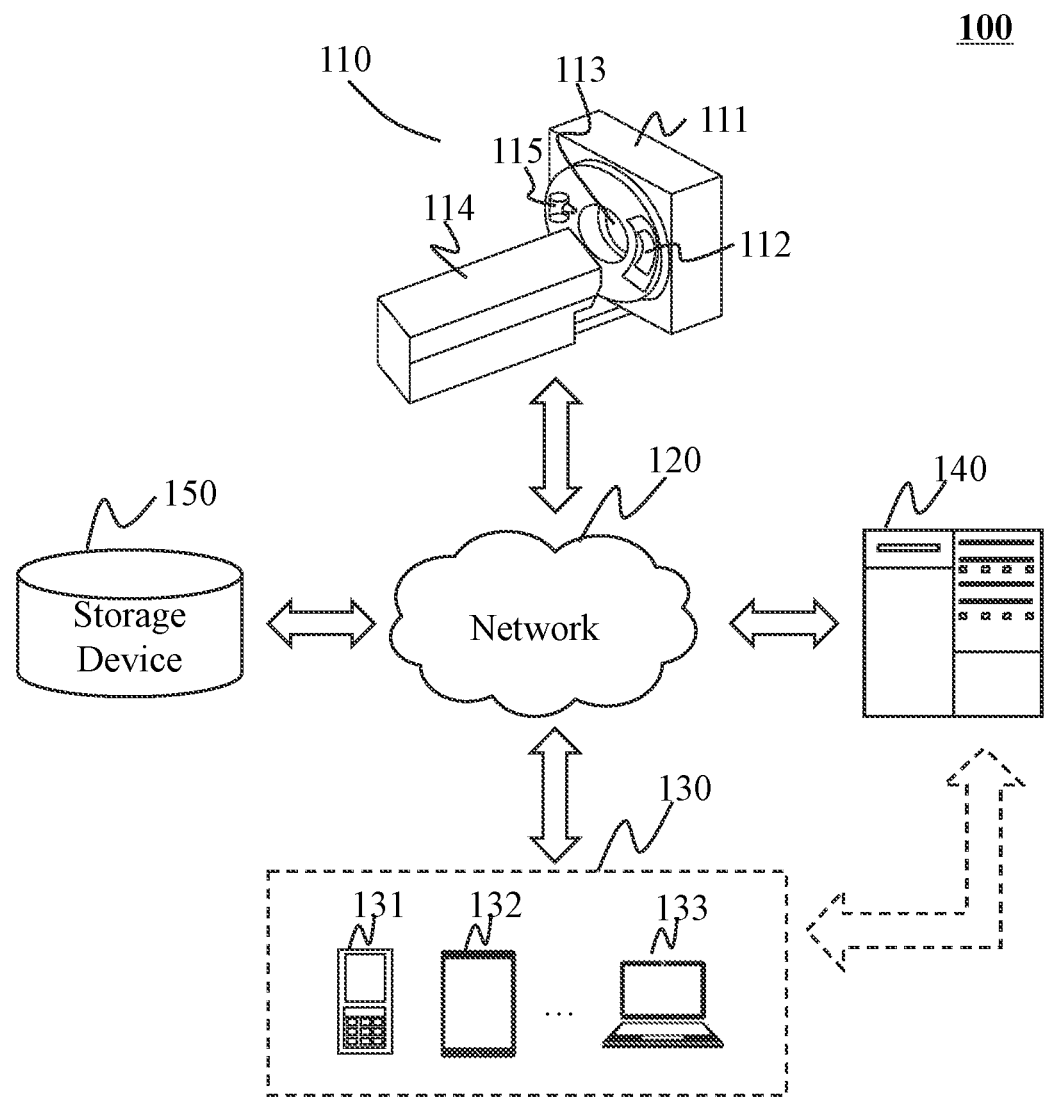
FIG. 1 is a schematic diagram illustrating an exemplary imaging system according to some embodiments of the present disclosure.

In order to more clearly illustrate the technical solutions related to the embodiments of the present disclosure, brief introduction of the drawings referred to the description of the embodiments is provided below. Obviously, drawings described below are only some examples or embodiments of the present disclosure. Those having ordinary skills in the art, without further creative efforts, may apply the present disclosure to other similar scenarios according to these drawings. Unless obviously obtained from the context or the context illustrates otherwise, the same numeral in the drawings refers to the same structure or operation.

It will be understood that the term "system," "engine," "unit," "module," and/or "block" used herein are one method to distinguish different components, elements, parts, sections, or assembly of different levels in ascending order. However, the terms may be displaced by another expression if they achieve the same purpose.

As used in the disclosure and the appended claims, the singular forms "a," "an," and "the" include plural referents unless the content clearly dictates otherwise. It will be further understood that the terms "comprise," "comprises," and/or "comprising," "include," "includes," and/or "including," when used in this specification, specify the presence of stated features, integers, steps, operations, elements, and/or components, but do not preclude the presence or addition of one or more other features, integers, steps, operations, elements, components, and/or groups thereof.

The flowcharts used in the present disclosure illustrate operations that systems implement according to some embodiments of the present disclosure. It is to be expressly understood the operations of the flowcharts may be implemented not in order. Conversely, the operations may be implemented in an inverted order, or simultaneously. Moreover, one or more other operations may be added to the flowcharts. One or more operations may be removed from the flowcharts.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

The method for obtaining a radiographic image disclosed in the present disclosure may be applied to a plurality of medical scanning imaging devices, including but not limited to, a computer radiography (CR), a digital radiography (DR), a computed tomography (CT) scanner, a screen X-ray machine, a mobile X-ray equipment (such as a mobile C-arm machine), a digital subtraction angiography (DSA) scanner, a linear accelerator, an emission computed tomography (ECT), or the like, or any combination thereof. Merely for the purpose of illustration, the detailed description regarding the technical solutions disclosed in the present disclosure is not intended to limit the scope of the present disclosure.

FIG. 1 is a schematic diagram illustrating an exemplary imaging system 100 according to some embodiments of the present disclosure.

The imaging system 100 may include an imaging device 110, a network 120, at least one terminal 130, a processing device 140, and a storage device 150. Each component of the system 100 may be connected to each other via the network 120. For example, the imaging device 110 and the at least one terminal 130 may be connected to or communicate with each other via the network 120.

In some embodiments, the imaging device 110 may include a radiographic device. For example, the imaging device 110 may be a radiation dynamic imaging device. As shown in FIG. 1, the imaging device 110 may include a gantry 111, a detector 112, a detection region 113, a scanning bed 114, and a radiation generating device 115. The gantry 111 may be configured to support the detector 112 and the radiation generating device 115. The subject may be placed on the scanning bed 114 for scanning. The subject may include a patient, a mold, or other subjects to be scanned. The scanning bed 114 may be parallel to the ground. The radiation generating device 115 may emit X-rays to the subject. By scanning the subject, the imaging device 110 may obtain scan data to generate (or reconstruct) an image.

The network 120 may include any suitable network that can facilitate the exchange of information and/or data of the imaging system 100. In some embodiments, at least one component of the imaging system 100 (e.g., the imaging device 110, the processing device 140, the storage device 150, at least one terminal 130) may exchange information and/or data with at least one other component of the imaging system 100 via the network 120. For example, the processing device 140 may obtain an output image from the imaging device 110 via the network 120. As another example, the processing device 140 may obtain user (e.g., a doctor) instructions from the at least one terminal 130 via the network 120. The network 120 may include a public network (e.g., the Internet), a private network (e.g., a local area network (LAN)), a wired network, a wireless network (e.g., an 802.11 network, a Wi-Fi network), a frame relay network, a virtual private network ("VPN"), a satellite network, a telephone network, routers, hubs, switches, server computers, or the like, or any combination thereof. For example, the network 120 may include a wireline network, an optical fiber network, a telecommunication network, a local area network, a wireless local area network (WLAN), a metropolitan area network (MAN), a public telephone switched network (PSTN), a Bluetooth™ network, a ZigBee™ network, a near field communication (NFC) network, or the like, or any combination thereof. In some embodiments, the network 120 may include one or more network access points. For example, the network 120 may include wired and/or wireless network access points, such as base stations and/or Internet exchange points, through which one or more components of the imaging system 100 may be connected to the network 120 to exchange data and/or information.

The at least one terminal 130 may communicate with and/or be connected with the imaging device 110, the processing device 140, and/or the storage device 150. For example, the at least one terminal 130 may obtain a detection image from the processing device 140. As another example, the at least one terminal 130 may obtain an output image obtained by the imaging device 110, and transmit the output image to the processing device 140 for processing. In some embodiments, the at least one terminal 130 may include a mobile device 131, a tablet computer 132, a laptop computer 133, or the like, or any combination thereof. For example, the mobile device 131 may include a mobile phone, a personal digital assistant (PDA), a gaming device, a navigation device, or the like, or any combination thereof. In some embodiments, the at least one terminal 130 may include an input device, an output device, etc. The input device may include alphanumeric and other keys. The input device may be input via a keyboard, a touch screen (for example, with haptics or tactile feedback), a speech input, an eye-tracking input, a brain monitoring system, or any other comparable input mechanism. The input information received through the input device may be transmitted to the processing device 140 via, for example, a bus, for further processing. Other types of input devices may include a cursor control device, such as a mouse, a trackball, or cursor direction keys, etc. The output device may include a display, a speaker, a printer, or the like, or any combination thereof. In some embodiments, the at least one terminals 130 may be part of the processing device 140.

The processing device 140 may process data and/or information obtained from the imaging device 110, the storage device 150, the at least one terminal 130, or other components of the imaging system 100. In some embodiments, the processing device 140 may obtain a control instruction for controlling the imaging device to image the subject. For example, the processing device 140 may obtain a control instruction for controlling the imaging device 110 to image the subject from the terminal 130. In some embodiments, the processing device 140 may determine target exposure parameters based on the control instruction, and image the subject based on the target exposure parameters to obtain the radiographic image. The target exposure parameters may be determined based on at least one parameter control curve, or biological information of the subject. In some embodiments, the processing device 140 may be a single server or a server group. The server group may be centralized or distributed. In some embodiments, the processing device 140 may be local to or remote from the imaging system 100. For example, the processing device 140 may access information and/or data from the medical device 110, the storage device 150, and/or the at least one terminal 130 via the network 120. As another example, the processing device 140 may be directly connected to the imaging device 110, the at least one terminal 130, and/or the storage device 150 to access information and/or data. In some embodiments, the processing device 140 may be implemented on a cloud platform. For example, the cloud platform may include a private cloud, a public cloud, a hybrid cloud, a community cloud, a distributed cloud, an inter-cloud, a multi-cloud, or the like, or any combination thereof. In some embodiments, the processing device 140 may be implemented by a computing device 200.

The storage device 150 may store data, instructions, and/or any other information. In some embodiments, the storage device 150 may store information reflecting a users behavior in using an imaging device. Specifically, the information reflecting a user's behavior in using an imaging device may include at least one of a parameter record of the imaging device manually adjusted by a user, a users satisfactory degree of an image output by the imaging device, a part to be imaged by a user using the imaging device, or a positioning area of a region of interest in an image output by the imaging device. In some embodiments, the storage device 150 may store data obtained from the imaging device 110, the at least one terminal 130, and/or the processing device 140. In some embodiments, the storage device 150 may store data and/or instructions that the processing device 140 may execute or use to complete exemplary methods described in the present disclosure. In some embodiments, the storage device 150 may include a mass storage device, a removable storage device, a volatile read-and-write storage, a read-only storage (ROM), or the like, or any combination thereof. Exemplary mass storage may include a magnetic disk, an optical disk, a solid-state drive, etc. Exemplary removable storage may include a flash drive, a floppy disk, an optical disk, a storage card, a zip disk, a magnetic tape, etc. Exemplary volatile read-and-write storage may include a random access storage (RAM). Exemplary RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. Exemplary ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage device 150 may be implemented on a cloud platform.

In some embodiments, the storage device 150 may be connected to network 120 to communicate with at least one other component of the imaging system 100 (e.g., the processing device 140, the at least one terminal 130). The at least one component of the imaging system 100 may access the data or instructions stored in the storage device 150 via the network 120. In some embodiments, the storage device 150 may be part of the processing device 140.

It should be noted that the above description is intended to be illustrative, and not to limit the scope of the present disclosure. For those skilled in the art, various variations and modifications can be made under the guidance of the present disclosure. The features, structures, methods, and other characteristics of the exemplary embodiments described herein may be combined in various ways to obtain additional and/or alternative exemplary embodiments. For example, the storage device 150 may be a data storage including cloud computing platforms, such as a public cloud, a private cloud, a community cloud, a hybrid cloud, etc. However, those variations and modifications do not depart from the scope of the present disclosure.

Figure 2:
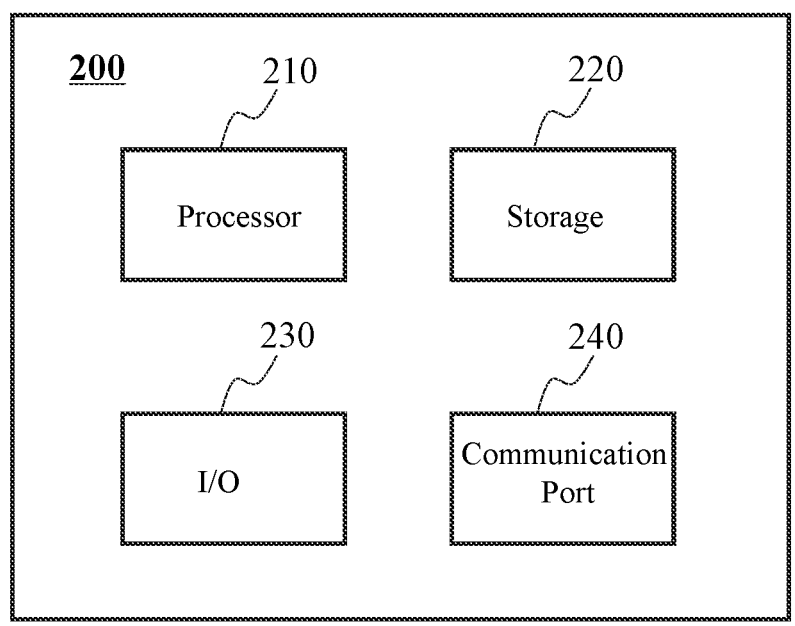
FIG. 2 is a schematic diagram illustrating exemplary hardware and/or software components of an exemplary computing device according to some embodiments of the present disclosure.

FIG. 2 is a schematic diagram illustrating exemplary hardware and/or software components of an exemplary computing device 200 according to some embodiments of the present disclosure.

The computing device 200 may include a processor 210, a storage 220, an input/output (I/O) 230, and a communication port 240.

The processor 210 may execute computer instructions (e.g., program code), and perform functions of the processing device 140 according to methods described herein. The computer instructions may include, for example, routines, programs, objects, components, data structures, procedures, modules, and functions, which perform particular functions described herein. For example, the processor 210 may process data obtained from the imaging device 110, the at least one terminal 130, the storage device 150, and/or any other component of the imaging system 100. In some embodiments, the processor 210 may include one or more hardware processors, such as a microcontroller, a microprocessor, a reduced instruction set computer (RISC), an application-specific integrated circuits (ASIC), an application-specific instruction-set processor (ASIP), a central processing unit (CPU), a graphics processing unit (GPU), a physics processing unit (PPU), a microcontroller unit, a digital signal processor (DSP), a field programmable gate array (FPGA), an advanced RISC machine (ARM), a programmable logic device (PLD), any circuit or processor capable of executing one or more functions, or the like, or any combinations thereof.

Merely for illustration, only one processor is described in the computing device 200. However, it should be noted that the computing device 200 in the present disclosure may also include a plurality of processors, and thus the operations and/or method operations that are performed by one processor as described in the present disclosure may also be jointly or separately performed by a plurality of processors. For example, if in the present disclosure the processor of the computing device 200 executes both operation A and operation B, it should be understood that operation A and operation B may also be performed by a plurality of different processors jointly or separately in the computing device 200 (e.g., a first processor executes operation A and a second processor executes operation B, or the first and second processors jointly execute operation s A and B).

The storage 220 may store data/information obtained from the imaging device 110, the at least one terminal 130, the storage device 150, and/or any other component of the imaging system 100. In some embodiments, the storage 220 may include a mass storage, a removable storage, a volatile read-and-write memory, a read-only memory (ROM), or the like, or any combination thereof. For example, the mass storage may include a magnetic disk, an optical disk, a solid-state drive, etc. The removable storage may include a flash drive, a floppy disk, an optical disk, a memory card, a zip disk, a magnetic tape, etc. The volatile read-and-write memory may include a random access memory (RAM). The RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. The ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage 220 may store at least one program and/or instruction to perform exemplary methods described in the present disclosure.

The input/output (I/O) 230 may be configured to input and/or output signals, data, information, or the like. In some embodiments, the I/O 230 may enable a user to interact with the processing device 140. In some embodiments, the I/O 230 may include an input device and an output device. Examples of the input device may include a keyboard, a mouse, a touch screen, a microphone, or the like, or any combination thereof. Examples of the output devices may include a display device, a loudspeaker, a printer, a projector, or the like, or any combination thereof. Examples of the display devices may include a liquid crystal display (LCD), a light-emitting diode (LED)-based display, a flat panel display, a curved screen, a television device, a cathode ray tube (CRT), or the like, or any combination thereof.

The communication port 240 may be connected to a network (e.g., the network 120) to facilitate data communications. The communication port 240 may establish connections between the processing device 140 and the imaging device 110, the at least one terminal 130, and/or the storage device 150. The connection may include a wired connection and a wireless connection The wired connection may include, for example, an electrical cable, an optical cable, a telephone wire, or the like, or any combination thereof. The wireless connection may include, for example, a Bluetooth™ link, a Wi-Fi™ link, a WiMax™ link, a WLAN link, a ZigBee™ link, a mobile network link (e.g., 3G, 4G, 5G), or the like, or any combination thereof. In some embodiments, the communication port 240 may be and/or include a standardized communication port, such as RS232, RS485, etc. In some embodiments, the communication port 240 may be specially designed. For example, the communication port 240 may be designed in accordance with the digital imaging and communications in medicine (DICOM) protocol.

FIG. 3 is a flowchart illustrating an exemplary process for obtaining a radiographic image according to some embodiments of the present disclosure. In some embodiments, the process 300 may be executed by processing logic, which may include hardware (e.g., circuits, dedicated logic, programmable logic, microcodes, etc.), software (instructions that run on a processing device to perform hardware simulation), or the like, or any combination thereof. In some embodiments, one or more operations in the process 300 for obtaining a radiographic image shown in FIG. 3 may be implemented by the processing device 140 shown in FIG. 1. In some embodiments, the one or more operations in the process 300 for obtaining a radiographic image shown in FIG. 3 may be implemented by a system 400 for obtaining a radiographic image shown in FIG. 4. For example, the process 100 may be stored in a storage device in the form of an instruction, and called and/or executed by the system 400 for obtaining a radiographic image. As shown in FIG. 3, the process 300 may include at least one operation below.

In 310, a control instruction for controlling an imaging device may be obtained to image a subject. In some embodiments, operation 310 may be executed by an obtaining module 410.

The control instruction may be an instruction that controls a radiographic device to radiate a target to be imaged and obtain a radiographic image. The control instruction may come from a control device of an imaging device, for example, a console or an exposure hand brake. The imaging device may include a medical radiographic device, an industrial detection radiation machine, a flaw detector, a security inspection device, or the like. The medical radiographic device may include, but is not limited to, a Computed Tomography (CT), a Single-Photon Emission Computed Tomography (SPECT), a Positron Emission Tomography (PET), a Digital Radiography (DR), a Computed Radiography (CR), a screen X-ray machine, a gastrointestinal machine, a Digital Subtraction Angiography (DSA), a mobile X-ray device (such as a mobile C-arm machine), a linear accelerator, or the like, or any combination thereof. Exemplary rays may include X-rays, gamma rays, beta rays, electron rays, proton beams, or the like, or any combination thereof. The rays passing through the object to be imagined may be detected, for example, in the form of projected data, by a detector of the imaging device. A radiographic image of the target to be imaged may be obtained by data processing (e.g., denoising, smoothing, enhancement, reconstruction, etc.).

In 320, target exposure parameters may be determined based on the control instruction. In some embodiments, operation 320 may be executed by a determination module 420.

In some embodiments, the target exposure parameters may refer to set parameters of a radiation generating device of the imaging device when a subject is imaged. For example, the setting parameters of the radiation generating device 115 of the imaging device 110. The exposure parameters may include a tube voltage, a tube current, an irradiation duration, etc. In some embodiments, the control instruction may include an indication for searching for exposure parameters imaging. The determination module 420 may first determine the target exposure parameters based on the parameter search indication in the control instruction.

In some embodiments, the exposure parameters may be determined based on at least a parameter control curve. The parameter control curve may be a curve reflecting a mapping relationship between the setting parameters of the radiation generating device. For example, the parameter control curve may reflect a curve composed of parameters that keep a brightness of an imaging image consistent under different imaging conditions (e.g., under different thickness conditions of the subject, under different imaging application scenarios). The mapping relationship between the setting parameters may include a mapping relationship between at least two of a tube voltage, a tube current, an irradiation duration, a product of a tube current and an irradiation duration, which may form a plurality of data pairs, and form the parameter control curve through curve fitting or a connection between points. Based on different imaging devices, the parameter control curve may include an Automatic Brightness Control (ABC) curve, an Automatic Brightness Stabilization (ABS) Curve, an Automatic Exposition Control (AEC) curve, or the like. In some embodiments, the parameter control curve may be a preset curve obtained based on long-term experience accumulation and optimization (which may be referred to as a first parameter control curve in the present disclosure), or may also be an optimized curve obtained by improving a preset curve according to operation data of the imaging device (for example, user operation data (which may be referred to as a second parameter control curve in the present disclosure).

In some embodiments, when obtaining the control instruction, the determination module 420 may pre-image the subject based on the control instruction, and obtain candidate exposure parameters based on a pre-imaging result and the parameter control curve. Subsequently, the determination module 420 may generate the target exposure parameters based on the candidate exposure parameters. The pre-imaging may be a prerequisite operation of imaging. For example, exposure may be imaging, and pre-imaging may be fluoroscopy. The determination module 420 may select at least one set of pre-imaging parameters (e.g., fluoroscopy parameters) from the parameter control curve, and then determine a target brightness of an imaging image. Subsequently, the determination module 420 may generate at least one pre-imaging image (e.g., a fluoroscopy image) based on at least one set of pre-imaging parameters. When a brightness of a certain fluoroscopy image is the same as the target brightness, pre-imaging parameters corresponding to the fluoroscopy image may be designated as candidate exposure parameters. After the candidate exposure parameters are determined, the determination module 420 may adjust the candidate exposure parameters to obtain target exposure parameters. For example, the determination module 420 may adjust at least one of the tube voltage, the tube current, and the irradiation duration of the candidate exposure parameters, such as multiplying, to obtain the target exposure parameters In the above description, the parameter control curve may be a first parameter control curve. It will be appreciated that habits of operators (for example, doctors) of the imaging device are different. Therefore, an image effect of a radiographic image obtained based on the first parameter control curve cannot meet the diagnostic habits of all clinicians. In addition, different clinicians may have different requirements for image quality according to their experience. For example, some doctors may be willing to lose part of the image quality to pursue lower radiation doses. For academic doctors, "high-quality" images may be their needs. Therefore, the parameter control curve may be a modified second parameter control curve, which may meet the operating habits of an operator (e.g., a doctor) of the imaging device. In some embodiments, the determination module 420 may obtain operation data of an imaging device. The operational data may at least include information reflecting a user's behavior in using the imaging device. For example, doctors adjustment data for the exposure parameters are automatically recorded by the imaging device when imaging. Subsequently, the determination module 420 may determine adjustment parameters of a radiation generating device in the imaging device according to the operation data. The adjustment parameters of the radiation generating device (e.g., an X-ray source) may include at least two of the tube voltage, the tube current, the irradiation duration, or a product of the tube current and an irradiation duration. For example, the determination module 420 may use commonly used exposure parameters saved by the user as the adjustment parameters. Thereafter, the determination module 420 may generate or correct the parameter control curve (i.e., a second parameter control curve) of the radiation generating device based on the adjustment parameters. For example, the determination module 420 may re-obtain a parameter control curve by using a regression method based on the adjustment parameters and the original data pair.

In some embodiments, the target exposure parameters may be determined based on at least biological information of the subject. A radiographic device (such as an X-ray machine, a computed tomography (CT), etc.) often has a problem with dose damage, so the dose is a parameter that must be strictly controlled in the radiographic imaging process. At the same time, the dose is also a decisive factor in image quality, and it is not as low as possible. Therefore, in radiography, it is necessary to determine the most appropriate value of the dose. The exposure parameters of an imaging device (e.g., a radiographic device) are related to a transmitted radiation dose. Appropriate exposure parameters may be obtained by determining an appropriate dose, which not only ensures low damage to a subject, but also high quality to a radiographic image.

In some embodiments, the determination module 420 may obtain a weight and an overall content of each component of the subject. For example, when the subject is a human body, a weight and an overall content of components such as water, fat, bone, and muscle, etc. that make up the human body may be obtained. Subsequently, the determination module 420 may determine each local component contained in the scanning part and the local content of each component of the local components according to the scanning part, the weight, and the overall content of each component of the subject. The component local content refers to a content of a certain component of the subject in the local area of the subject. For example, when the scanning part is a chest, the local components are the local content of each local component such as bones, muscle, water, fat, etc., which may be determined according to the weight and the overall content of each component of the subject, such as a statistical table obtained from big data or a constructed model. Thereafter, the determination module 420 may determine total attenuation information corresponding to the scanning part according to component attenuation information of each of the local components to a preset ray spectrum and the component local content of the corresponding local component. The preset ray spectrum may include a spectrum of a ray source used for imaging, for example, a ray spectrum. The component attenuation information refers to the attenuation of a certain component to the irradiated radiation spectrum, for example, an attenuation amount. After the total attenuation information is determined, the determination module 420 may determine the dose corresponding to the scanning part according to the total attenuation information. For example, according to the total attenuation information, and a mapping table between the attenuation information and a set dose, the dose corresponding to the scanning part may be determined by looking up the table. Finally, according to the relationship between the dose and the exposure parameters, such as a mapping table, etc., the determination module 420 may determine the target exposure parameters.

Other descriptions regarding determining the target exposure parameters may be found in FIG. 5-FIG. 15 of the present disclosure.

In 330, based on the target exposure parameters, the subject may be imaged to obtain the radiographic image. In some embodiments, operation 330 may be executed by an imaging module 430.

In some embodiments, the imaging module 430 may perform parameter settings on the radiation generating device based on the determined target exposure parameters according to the imaging indication in the control instruction, and deliver radiation to the subject to obtain the radiographic image.

It should be noted that the above description of the process 100 is merely provided for illustration and not intended to limit the scope of the present disclosure. For those skilled in the art, various modifications and changes may be conducted to the process 100 under the teaching of the present disclosure. However, these modifications and changes are still within the scope of the present disclosure.

Figure 4:
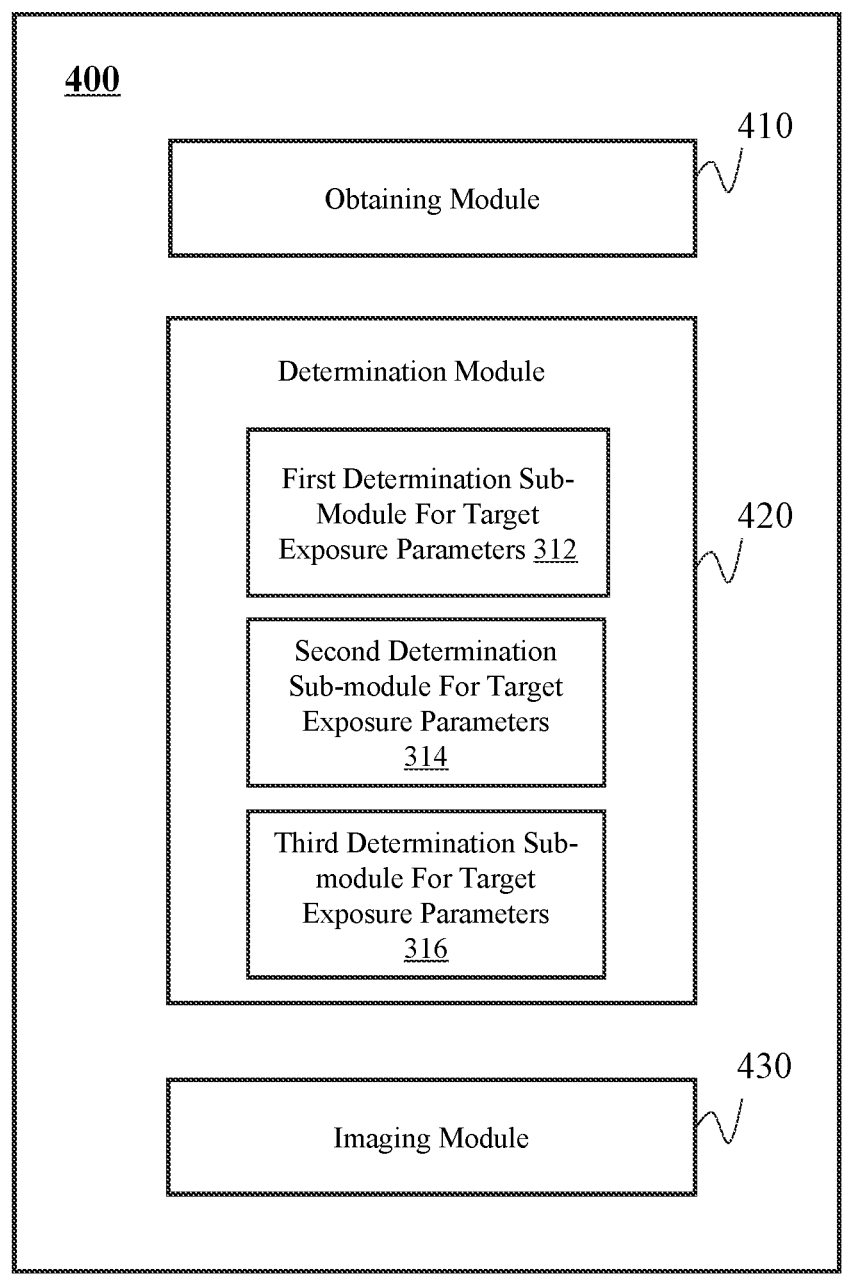
FIG. 4 is a block diagram illustrating an exemplary system for obtaining a radiographic image according to some embodiments of the present disclosure.

FIG. 4 is a block diagram illustrating an exemplary system 400 for obtaining a radiographic image according to some embodiments of the present disclosure. As shown in FIG. 4, the system 400 for obtaining a radiographic image may include an obtaining module 410, a determination module 420, and an imaging module 430.

The obtaining module 410 may be configured to obtain. The control instruction may be an instruction that controls a radiographic device to radiate a target to be imaged and obtain a radiographic image, which may come from a control device of an imaging device, such as a console or an exposure hand brake.

The determination module 420 may determine the target exposure parameters based on the control instruction. The target exposure parameters refer to set parameters of the radiation generating device of the imaging device when the subject is scanned, which may include a tube current, a tube voltage, an irradiation duration, or the like. In some embodiments, the exposure parameters may be determined based on at least one parameter control curve. The determination module 420 may pre-image the subject based on the control instruction after the control instruction is obtained, and obtain candidate exposure parameters based on a pre-imaging result and the parameter control curve. Subsequently, the determination module 420 may generate the target exposure parameters based on the candidate exposure parameters. The determination module 420 may also obtain operation data of the imaging device, and determine adjustment parameters of the radiation generating device in the imaging device according to the operation data, and then generate or correct the parameter control curve of the radiation generating device based on the adjustment parameters.

In some embodiments, the target exposure parameters may be determined based on at least biological information of the subject. The determination module 420 may obtain a weight and an overall content of each component of the subject, and determine each local component contained in the scanning part, and the local content of each component of the local components according to the scanning part, the weight, and the overall content of each component of the subject. The determination module 420 may also determine total attenuation information corresponding to the scanning part according to component attenuation information of each of the local components to a preset ray spectrum and the component local content of the corresponding local component. After the total attenuation information is determined, the determination module 420 may determine a dose corresponding to the scanning part according to the total attenuation information. Finally, the determination module 420 may determine the target exposure parameters according to a relationship between the dose and the exposure parameters, such as a mapping table, etc. In some embodiments, the determination module 420 may further include a first determination sub-module for target exposure parameters 312, a second determination sub-module for target exposure parameters 314, and a third determination sub-module for target exposure parameters 316. More descriptions regarding these three sub-modules may be found elsewhere in the present disclosure. See, e.g., FIG. 6, FIG. 10, and FIG. 14 and relevant descriptions thereof.

The imaging module 430 may image the subject based on the target exposure parameters to obtain the radiographic image. In some embodiments, the imaging module 430 may perform parameter setting based on the determined target exposure parameters according to an imaging indication in the control instruction, and deliver radiation to the subject to obtain the radiographic image.

It should be understood that the system and modules shown in FIG. 4 may be implemented in various ways. For example, in some embodiments, the system and its modules thereof may be implemented by hardware, software, or a combination of software and hardware. The hardware may be implemented by a specific logic. The software may be stored in a storage and executed by an appropriate instruction execution system, such as a microprocessor dedicated design hardware. It will be understood by those skilled in the art that the above-mentioned methods and systems may be implemented using computer-executable instructions and/or embedded in control codes of a processor. For example, the control codes may be provided by a carrier medium, such as a disk, a CD, or a DVD-ROM, a programmable storage such as a read-only memory (firmware), or a data carrier such as an optical carrier or an electronic signal carrier. The system and its modules thereof of the present disclosure may be implemented by a hardware circuit such as a super large-scale integrated circuits or a gate arrays, a semiconductor such as a logic chip, a transistor, etc., or a programmable hardware device such as a field programmable gate array, a programmable logic device, etc. The system and its modules thereof may be implemented by software that can be executed by various processors or may be implemented by a combination (e.g., firmware) of the hardware circuit and the software.

It should be noted that the above description of the candidate item display and determination system and modules is merely provided for the purposes of illustration, and not intended to limit the scope of the present disclosure. It will be understood that for those skilled in the art, after understanding the principle of the system, it is possible to arbitrarily combine various modules, or form subsystems to connect with other modules without departing from this principle. For example, in some embodiments, for example, the obtaining module 410, the determination module 420, and the imaging module 430 disclosed in FIG. 2 may be different modules in a system, or one module implementing functions of two or more modules mentioned above. For example, the obtaining module 410 and the determination module 420 may be two modules, or one module having a function of obtaining instructions and determining parameters at the same time. As another example, each module may share a storage module. Each module may have its own storage module. Those variations are still within the scope of the present disclosure.

Figure 5:
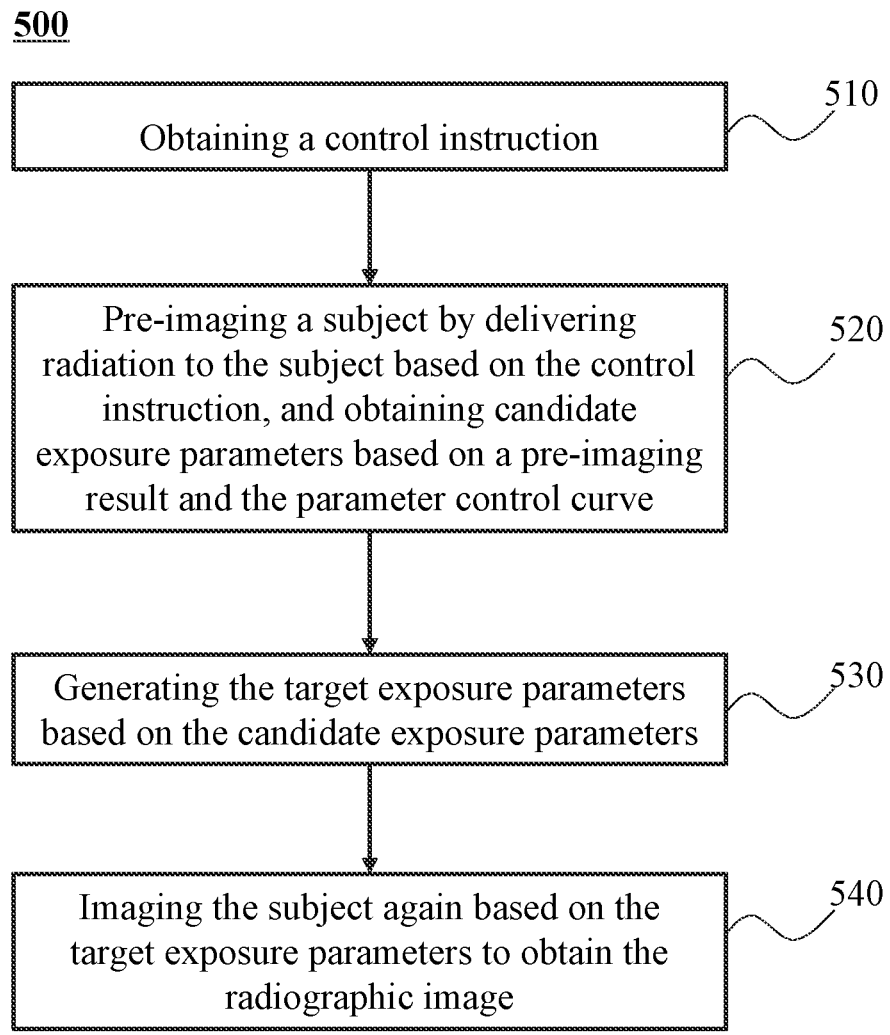
FIG. 5 is a flowchart illustrating an exemplary process for obtaining a radiographic image according to some embodiments of the present disclosure.

FIG. 5 is a flowchart illustrating an exemplary process for obtaining a radiographic image according to some embodiments of the present disclosure. In some embodiments, the process 500 may be executed by processing logic, which may include hardware (e.g., circuits, dedicated logic, programmable logic, microcodes, etc.), software (instructions that run on a processing device to perform hardware simulation), or the like, or any combination thereof. One or more operations shown in the process 500 for obtaining a radiographic image shown in FIG. 5 may be implemented by a system 600 for obtaining a radiographic image shown in FIG. 6. For example, the process 500 may be stored in a storage device in the form of an instruction and called and/or executed by a processing device 600. As shown in FIG. 5, the process 500 may include at least one operation below.

In 510, a control instruction may be obtained. In some embodiments, operation 510 may be executed by the obtaining module 410.

In some embodiments, the control instruction may be obtained at the first time. The first time refers to any time when the target to be imaged in a complete related process. Merely for illustration, assuming that a target to be imaged is a patient, a process related to the patient may include a process including diagnosis, treatment, rehabilitation, etc. The first time may include any time point in the patient's diagnosis, preoperative, intraoperative, postoperative, and recovery period. As another example, assuming that the target to be imaged is a material, a process related to the material may include a process including detection, repair, post-repair confirmation, or the like. The first time may be any time point in the material undergoes flaw detection, defect repair, and post-repair confirmation. In some embodiments, the first time may be a time at which a patient is during surgery.

In some embodiments, the control instruction may be an instruction that controls a radiographic device to radiate a target to be imaged and obtain a radiographic image, which may come from a control device of an imaging device. The control instruction may come from an exposure hand brake, such as an exposure control device of a radiographic device. The radiographic device may include a medical radiographic device, an industrial detection radiation machine, a flaw detector, a security inspection device, or the like. The medical radiographic device may include but is not limited to a Computed Tomography (CT), a Single-Photon Emission Computed Tomography (SPECT), a Positron Emission Tomography (PET), a Digital Radiography (DR), a Computed Radiography (CR), a screen X-ray machine, a gastrointestinal machine, a Digital Subtraction Angiography (DSA), a mobile X-ray device (such as a mobile C-arm machine), a linear accelerator, or the like, or any combination thereof. Preferably, the medical radiographic device may be a C-arm machine. Exemplary rays may include X-rays, gamma rays, beta rays, electron rays, proton beams, or the like, or any combination thereof. The rays passing through the object to be imagined may be detected, for example, in the form of projected data, by a detector of the imaging device. A radiographic image of the target to be imaged may be obtained by data processing (e.g., denoising, smoothing, enhancement, reconstruction, etc.).

In some embodiments, the control instruction may include a pre-imaging start indication and an imaging start indication. Pre-imaging refers to a process in which at least one image is formed by loading an appropriate amount of radiation on the target to be imaged to determine or search for appropriate pre-imaging exposure parameters or exposure parameters. The image obtained during the pre-imaging process refers to as a pre-imaging image. The imaging refers to a process of image acquisition of the target to be imaged based on pre-imaging exposure parameters of the pre-imaging process based on the exposure parameters determined during the pre-imaging process. Imaging exposure parameters used during imaging may be the same as or different from the pre-imaging exposure parameters. The image obtained after the completion of the imaging process may be retained and archived as the official or final imaging result of the target to be imaged, may be used as a reference for other parts of the related process, or be kept as a file in the process. In some embodiments, the pre-imaging may be fluoroscopy, the imaging may be a single-frame image acquisition. In some embodiments, the control instruction may be input by a user (e.g., a doctor) of a radiographic device. For example, a doctor may click on an image acquisition button on the control console of a radiographic device to send a control instruction. After receiving the control instruction, the processing device such as the system 600 for obtaining a radiographic image may start pre-imaging and the imaging process based on a start indication included in the control instruction.

In 520, a subject may be pre-imaged by delivering radiation to the subject based on the control instruction, and candidate exposure parameters may be obtained based on a pre-imaging result and the parameter control curve. In some embodiments, operation 520 may be performed by the determination module 420 (e.g., a parameter determination unit 610 in the first determination sub-module for target exposure parameters 312).

In some embodiments, the subject refers to an object to be imaged, including a patient, a body model, an industrial material, an item to be inspected, or the like. The subject also refers to a part or an organ of a patient, such as a head, a chest, an abdomen, limbs, or the like. The candidate exposure parameters may be pre-imaging exposure parameters when a difference between a brightness of a pre-imaging image and a first target brightness satisfies a preset condition. The first target brightness refers to a brightness of a pre-imaging image to achieve a desired definition. In some embodiments, the first target brightness may be pre-stored in the system 600 for obtaining a radiographic image, or input by a user, or adjusted according to different application scenarios, which is not limited in the present disclosure.

During the pre-imaging process, the system 600 for obtaining a radiographic image may obtain at least one frame of a pre-imaging images (e.g., 3 to 5 frames), and each pre-imaging image has different image brightness due to difference exposure parameters. In general, exposure parameters may include a tube voltage, a tube current, an irradiation duration, or the like. The tube refers to a radiation source tube, for example, an X-ray tube. The tube voltage refers to a voltage applied between two poles of the ray tube to form a particle (e.g., an electron) accelerometer filed, and determine the intensity of the ray (or photon energy). The tube current refers to an accelerated particle beam (for example, an electron beam). The tube current is determined by a tube voltage and a current of the radiation tube. The irradiation duration refers to the duration of radiation emission. A product of a tube current and an irradiation duration determines a count of rays (or a count of photons). A product of a tube voltage, a tube current, and an irradiation duration determines energy input to a tube. Since the energy of the radiation emitted by different pre-imaging exposure parameters is different, the energy of the radiation received by the radiation detector after passing through the subject is also different, and the brightness of the formed image is also different. In some embodiments, a brightness of a pre-imaging image may be subtracted from the first target brightness to obtain a difference between the two, which may be designated as the difference. The preset condition means that an absolute value of the difference does not exceed a preset brightness difference threshold, such as 1, 5, 10, or the like. When the preset condition is satisfied, pre-imaging exposure parameters used to form a pre-imaging image of the brightness may be designated as the candidate exposure parameters. In some embodiments, the candidate exposure parameters may include a first tube voltage, a first tube current, and a first irradiation duration.

Figures 8, 9:
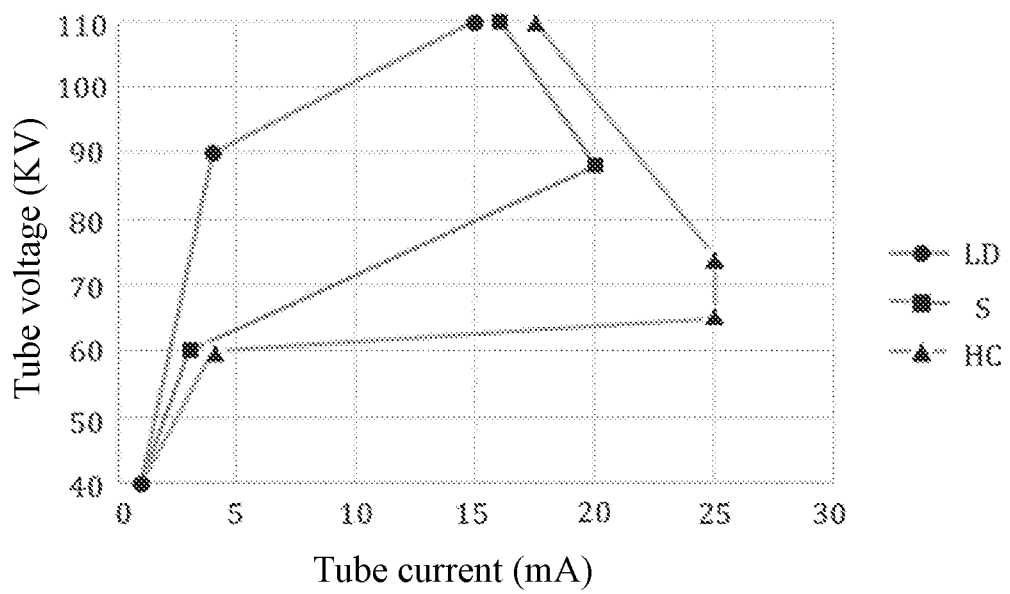
FIG. 8 is a flowchart illustrating an exemplary process for determining target exposure parameters according to some embodiments of the present disclosure.
FIG. 9 is a schematic diagram illustrating an exemplary ABS curve according to some embodiments of the present disclosure.

In some embodiments, the candidate exposure parameters may be determined based on a comparison result between a brightness of a pre-imaging image and a first target brightness, and an automatic brightness stabilization (ABS) curve. The ABS curve refers to a curve composed of parameters that maintain image brightness consistency under different conditions (e.g., under different thickness conditions, under different application scenarios) under a premise of ensuring image quality requirements. See FIG. 9. FIG. 9 is a schematic diagram illustrating an exemplary ABS curve according to some embodiments of the present disclosure. As shown in FIG. 9, the abscissa of the ABS curve is a tube current in mA, and the ordinate is a tube voltage in kV. Expose with the parameters indicated by the points on the same curve. For the same subject (that is, the body thickness does not change) and the same irradiation duration, an image brightness obtained by exposure parameters corresponding to upper points on the curve is greater than that obtained by exposure parameters corresponding to lower points on the curve. It will be understood that if the brightness needs to be kept unchanged, under one same irradiation duration, points on the curve corresponding to exposure parameters used for a subject with a smaller thickness are lower than points on the curve corresponding to exposure parameters used for a subject with a larger thickness. Similarly, the ABS curve may also reflect a change relationship between the exposure parameters (for example, a tube voltage, a tube current, and a current time product (a product of a tube current and an irradiation duration)) used in order to keep the image brightness unchanged in the case of different subjects (that is, different body thicknesses) with different irradiation duration. The ABS curve shown in FIG. 9 contains 3 curves, which respectively correspond to different application requirements. Since a tube current and an irradiation duration have equivalent contributions to a radiation dose, for simplicity, the curve shown in FIG. 9 uses the tube current as of the variable parameter. LD denotes low dose, i.e., a low dose mode. This mode reduces the radiation dose compared to a standard mode. Parameters affecting an image brightness may include a tube voltage, a tube current, and an irradiation duration. An increase in the tube voltage may result in an increase in the penetration of the rays, so that the count of rays passing through the subject to a radiation detector of a radiographic imaging device may increase, and at the same time, the count of rays absorbed by the subject (for example, a human body) may be reduced. Therefore, in order to maintain the same brightness at different thicknesses, the tube voltage may be greatly increased or decreased, and the tube current may be slightly increased or decreased to achieve a purpose of maintaining brightness. S denotes standard, i.e., a standard mode. The curve can meet most application requirements, and the radiation dose absorbed by the human body under the conditions of ensuring brightness tends to be moderate. HO denotes high contrast, i.e., a high contrast mode. High contrast means that a required image needs to have high contrast, so there is a need for a larger tube current and a longer irradiation duration.

See FIG. 5 again. In some embodiments, the system 600 for obtaining a radiographic image may take any point on the ABS curve as an initial pre-imaging exposure parameter to expose the subject and obtain a brightness of a pre-imaging image. Then, the difference between the brightness of the pre-imaging image and the first target brightness may be determined. Based on a comparison result (for example, the brightness of the pre-imaging image is less than a first target brightness, and the brightness of the pre-imaging image is greater than a first target brightness), the system 600 for obtaining a radiographic image may search for an exposure parameter corresponding to a next point along the ABS curve (for example, move down or up along the curve) to perform a next imaging, and compare the brightness of the retrieved pre-imaging image with the first target brightness until a difference between the brightness of the pre-imaging image and the first target brightness meets a preset condition. The pre-imaging parameters at this time may be used as the candidate exposure parameters. Detailed descriptions regarding obtaining candidate exposure parameters may be found elsewhere in the present disclosure (e.g., FIG. 7), which will not be repeated herein.

In 530, the target exposure parameters may be generated based on the candidate exposure parameters. In some embodiments, operation 530 may be performed by the determination module 420 (e.g., a parameter determination unit 610 in the first determination sub-module for target exposure parameters 312).

It will be appreciated that in some embodiments, the count of radiation delivered to the subject during the pre-imaging process may be small, and the single-frame radiographic image to be obtained by the imaging process may require high-definition requirements, so the count of radiation delivered to the subject is relatively large. Based on this, the system 600 for obtaining a radiographic image may first determine target exposure parameters based on the candidate exposure parameters, and then perform imaging on the subject delivering radiation based on the target exposure parameters to obtain a radiographic image of the subject.

Similar to the candidate exposure parameters, the target exposure parameters may include a second tube voltage, a second tube current, and a second irradiation duration. The system 600 for obtaining a radiographic image may adjust at least one of a first tube voltage, a first tube current, or a first irradiation duration in the candidate exposure parameters to obtain the target exposure parameters. In some embodiments, the first tube voltage may be directly designated as the second tube voltage, i.e., the tube voltage is kept unchanged. The first tube current may be increased by a first increment to obtain the second tube current. The first irradiation duration may be directly designated as the second irradiation duration. In some embodiments, the first tube voltage may be directly designated as the second tube voltage. The first tube current may be directly designated as the second tube current. The first irradiation duration may be increased by a second increment to obtain the second irradiation duration. In some embodiments, the first tube voltage may be directly designated as the second tube voltage. The first tube current may be increased by a third increment to obtain the second tube current. The first irradiation duration may be increased by a fourth increment to obtain the second irradiation duration. The first, second, third, and fourth increments may be determined based on the brightness of the radiographic image required during the imaging process and the first target brightness. For example, assuming that the brightness of the radiographic image required in the imaging process is A, the first target brightness is B, the amount of radiation required during the imaging process is NB times the amount of radiation emitted during the pre-imaging process. Therefore, if the tube voltage is constant, a product of the second tube current and the second irradiation duration is NB times a product of the first tube current and the first irradiation duration. Based on the above relationship, the first, second, third, and fourth increments may be determined. The first, second, third, and fourth increments may also be preset values of a processing device such as the system 600 for obtaining a radiographic image, or may be a value input by a user (e.g., a doctor), which will not be limited in the present disclosure.

In some embodiments, a parameter determination model may be utilized to determine the target exposure parameters. The parameter determination model may be obtained after training from a plurality of sample data pairs. A sample data pair may include an exposure parameter, a body thickness of a subject to be imaged, and a brightness of a corresponding obtained imaging image. The exposure parameters used may include a tube voltage, a tube current, an irradiation duration, and a relationship between a tube voltage, a tube current, and an irradiation duration may obey an ABS curve. For example, an exposure parameter indicated by a point on the ABS curve and the image brightness maintained under different thicknesses may be used as a sample data pair. In some embodiments, the parameter determination model may be a plurality of fitting functions obtained by function fitting based on sample data pairs, or a trained statistical model based on sample data pairs, for example, a multiple regression model, or a machine learning model, such as a neural network model. In some embodiments, the parameter determination model may be obtained by the determination module 420 (e.g., a model obtaining unit 620 in the first determination sub-module for target exposure parameters 312). The parameter determination model may determine the remaining value based on any two values between the input exposure parameters, thickness, and image brightness. For example, the parameter determination model may determine the brightness of the image obtained by imaging based on the exposure parameters and the body thickness. In some embodiments, the parameter determination model may include a general model or a plurality of sub-models. After the candidate exposure parameters are determined, a body thickness of the subject may be determined by inputting the candidate exposure parameters and the first target brightness into the parameter determination model. After the thickness of the subject is determined, the target exposure parameters may be obtained by inputting the body thickness of the subject and a brightness of a radiographic image (such as a second target brightness) required by the imaging process. Specific descriptions regarding obtaining target exposure parameters may be found elsewhere in the present disclosure (e.g., FIG. 8), which will not be repeated herein.

In 540, the subject may be imaged again based on the target exposure parameters to obtain the radiographic image. In some embodiments, operation 530 may be performed by the imaging module 430.

In some embodiments, the imaging module 430 may set parameters of the radiation generating device based on the determined target exposure parameters according to an imaging indication in the control instruction, and deliver radiation to the subject to obtain a radiographic image.

In some embodiments, the system 600 for obtaining a radiographic image may directly deliver radiation to the subject based on the candidate exposure parameters to obtain a radiographic image. For example, under the principle of low requirements on the radiographic images obtained during the imaging process, or the combination of the small amount of radiation in the pre-imaging process and the high quality of the radiographic images obtained during the imaging process, the subject may be imaged directly based on the candidate exposure parameters.

It should be noted that the above description of the process 500 is merely provided for illustration and not intended to limit the scope of the present disclosure. For those skilled in the art, various modifications and changes may be conducted to the process 500 under the teaching of the present disclosure. However, these modifications and changes are still within the scope of the present disclosure. For example, operation 520 may be divided into a brightness contrast process and a process of obtaining candidate exposure parameters.

Figure 6:
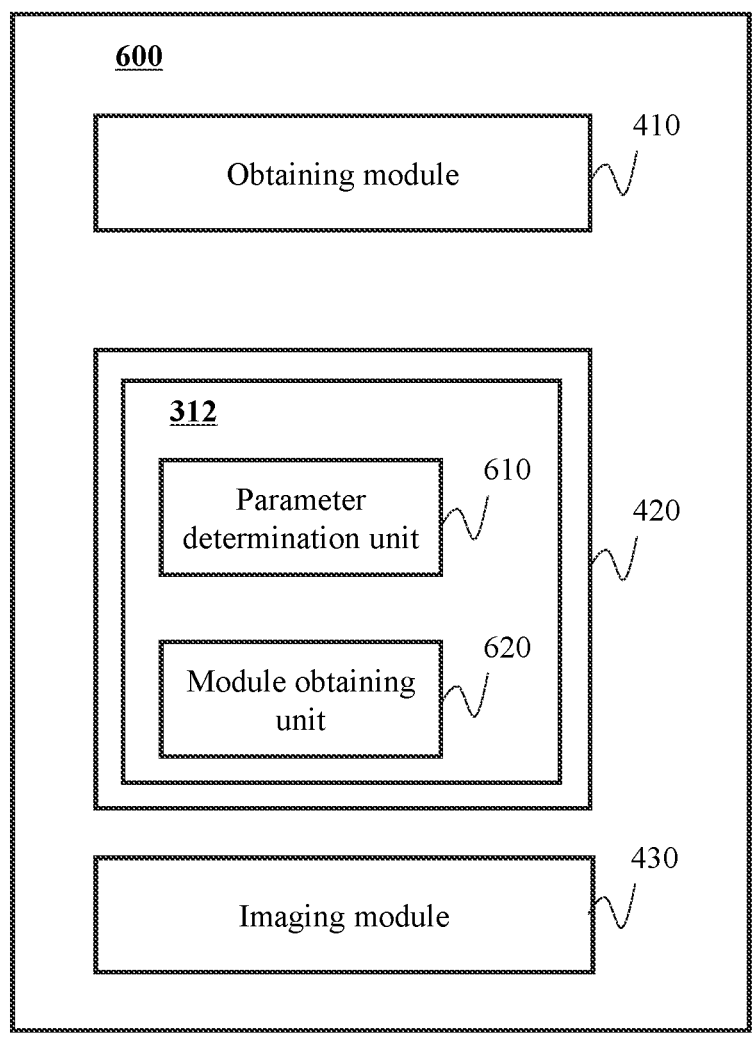
FIG. 6 is a block diagram illustrating an exemplary first determination sub-module for target exposure parameters of a system for obtaining a radiographic image according to some embodiments of the present disclosure.

FIG. 6 is a block diagram illustrating a system 600 for obtaining a radiographic image according to some embodiments of the present disclosure. As shown in FIG. 6, a processing module 600 may include the obtaining module 410, the determination module 420, and an imaging module 430. The first determination sub-module for target exposure parameters 312 in the determination module 420 may further include a parameter determination unit 610 and a module obtaining unit 620.

The obtaining module 410 may receive a control instruction. The obtaining module 410 may obtain the control instruction at a first time. The first time refers to any time when the target to be imaged is in an entire related process. Merely for illustration, assuming that a target to be imaged is a patient, a process related to the patient may include a process including diagnosis, treatment, rehabilitation, etc. The first time may include any time point in the patient's diagnosis, preoperative, intraoperative, postoperative, and recovery period. The control instruction may be an instruction that controls a radiographic device to radiate a target to be imaged and obtain a radiographic image, which may include a pre-imaging initiation indication and an imaging initiation indication. Pre-imaging refers to a process in which at least one image is formed by loading an appropriate amount of radiation on the target to be imaged to determine or search for appropriate pre-imaging exposure parameters or exposure parameters. The imaging refers to a process of image acquisition of the target to be imaged based on pre-imaging exposure parameters of the pre-imaging process or based on the exposure parameters determined by the pre-imaging process.

The determination module 420 (or the parameter determination unit 610 in the first determination sub-module for target exposure parameters 312) may pre-image the subject by delivering radiation to the subject based on the control instruction to obtain candidate exposure parameters based on the pre-imaging result and the parameter control curve. In some embodiments, the determination module 420 (or the parameter determination unit 610 in the first determination sub-module for target exposure parameters 312) may obtain the pre-imaging exposure parameters, and the brightness of at least one frame pre-imaging image, and compare the brightness with the preset first target brightness. After obtaining the comparison result, the determination module 420 (or the parameter determination unit 610 in the first determination sub-module for target exposure parameters 312) may update the pre-imaging exposure parameter based on the comparison result and the ABS curve, so that the difference between the pre-imaging image brightness and the first target brightness may meet a preset condition, and may use the updated pre-imaging exposure parameters as the candidate exposure parameters. The pre-imaging exposure parameters refer to the preset exposure parameters used in the pre-imaging process of the subject, including a tube current, a tube voltage, an irradiation duration, or the like. The determination module 420 (or the parameter determination unit 610 in the first determination sub-module for target exposure parameters 312) may compare the value of the brightness of the image (e.g., a pre-imaging image) obtained by using preset exposure parameters with the value of the first target brightness to obtain a comparison result, including that the brightness of the pre-imaging image is less than the first target brightness, the brightness of the pre-imaging image is equal to the first target brightness, or the brightness of the pre-imaging image is greater than the first target brightness. When the brightness of the pre-imaging is less than the first target brightness, the determination module 420 (or the parameter determination unit 610 in the first determination sub-module for target exposure parameters 312) may go upward along (for example, the direction in which the abscissa or the ordinate increases) the ABS curve to determine the next point. When the brightness of the pre-imaging is greater than the first brightness, the determination module 420 (or the parameter determination unit 610 in the first determination sub-module for target exposure parameters 312) may move downward along (for example, the direction in which the abscissa or the ordinate decreases) the ABS curve to determine the next point. After re-determining a point and its corresponding exposure parameters (e.g., a tube voltage and a tube current), the determination module 420 (or the parameter determination unit 610 in the first determination sub-module for target exposure parameters 312) may control the radiographic imaging device to obtain a new pre-imaging image of the subject and its corresponding image brightness based on the updated pre-imaging exposure parameters, and compare with the first target brightness again to obtain a comparison result. The above process may be repeated until the difference between the brightness of the updated pre-imaging image and the first target brightness meets the preset condition. When the difference satisfies the preset condition, the updated pre-imaging exposure parameters may be used as the candidate exposure parameters. The difference refers to the difference between the value of the brightness of the pre-imaging image and the value of the first target brightness. The preset condition means that the absolute value of the difference between the above two brightness values is less than or equal to a brightness difference threshold. When the brightness of the pre-imaging image is equal to the first target brightness, the determination module 420 (or the parameter determination unit 610 in the first determination sub-module for target exposure parameters 312) may directly use the pre-imaging exposure parameters as the candidate exposure parameters. In some embodiments, the determination module 420 (or the parameter determination unit 610 in the first determination sub-module for target exposure parameters 312) may transform the data included in the candidate exposure parameters to obtain the target exposure parameters, for example, changing at least one of a tube voltage, a tube current, or an irradiation duration. In some embodiments, the determination module 420 (or the parameter determination unit 610 in the first determination sub-module for target exposure parameters 312) may determine the equivalent thickness of the subject based on candidate exposure parameters and the first target brightness, and determine the target exposure parameter based on the equivalent thickness of the subject and the second target brightness. The determination module 420 (or the parameter determination unit 610 in the first determination sub-module for target exposure parameters 312) may input the candidate exposure parameters and the first target brightness into the brightness-thickness-parameter model to obtain the equivalent thickness of the target object, and input the equivalent thickness of the subject and the second target brightness into the brightness-thickness-parameter model to obtain the target exposure parameters. The target exposure parameters may include a second tube voltage, a second tube current, a second irradiation duration, or the like.

The determination module 420 (or the model obtaining unit 620 in the first determination sub-module for target exposure parameters 312) may obtain a brightness-thickness-parameter model. The determination module 420 (or the model obtaining unit 620 in the first determination sub-module for target exposure parameters 312) may obtain the exposure parameters corresponding to the test targets of different thicknesses when the image brightness reaches a plurality of different brightness. The exposure parameters may include a tube voltage, a tube current, an irradiation duration, etc. The corresponding points of tube voltage and tube current are on the ABS curve. Thereafter, the determination module 420 (or the model obtaining unit 620 in the first determination sub-module for target exposure parameters 312) may determine a plurality of fitting functions at different brightness between a plurality of test target thicknesses and corresponding exposure parameters, and use the fitting functions as the brightness-thickness-parameter model. Alternatively, the determination module 420 (or the model obtaining unit 620 in the first determination sub-module for target exposure parameters 312) may train the initial model to obtain a trained brightness-thickness-parameter model based on the thickness of the plurality of test targets, the exposure parameters, and the brightness of the corresponding image. The initial model shown may be a statistical model, such as a multi-regression model, or a machine learning model, for example, a neural network model. The determination module 420 (or the model obtaining unit 620 in the first determination sub-module for target exposure parameters 312) may also use a statistical model obtained after statistical analysis of a plurality of thicknesses, brightness, and corresponding exposure parameter data as the brightness-thickness-parameter model. The brightness-thickness-parameter model may be pre-determined and stored in a storage device (for example, an internal storage of the system 600 for obtaining a radiographic image, or an external storage device connected to the system 600 for obtaining a radiographic image via a wired or wireless connection). The model obtaining module 240 may communicate with the storage device to obtain the brightness-thickness-parameter model. The brightness-thickness-parameter model may also be obtained by the determination module 420 (or the model obtaining unit 620 in the first determination sub-module for target exposure parameters 312) after performing statistical analysis on the obtained image brightness of test targets of different thicknesses and the corresponding exposure parameters when the brightness reaches a plurality of different brightness.

The imaging module 430 may use the determined exposure parameters (e.g., candidate exposure parameters or target exposure parameters) to perform imaging the subject delivering radiation to obtain a radiographic image of the subject. Under the principle of low requirements on the radiographic images obtained during the imaging process, or the combination of the small amount of radiation in the pre-imaging process and the high quality of the radiographic images obtained during the imaging process, the imaging module 430 may directly image the subject based on the candidate exposure parameters. As another example, under the conditions that need to meet high requirements, the imaging module 430 may image the subject based on the target exposure parameters determined by other components (e.g., the determination module 420) of the system 600 for obtaining a radiographic image.

It should be understood that the system and its modules shown in FIG. 6 may be implemented in various ways. For example, in some embodiments, the system and its modules thereof may be implemented by hardware, software, or a combination of software and hardware. The hardware may be implemented by a specific logic. The software may be stored in a storage and executed by an appropriate instruction execution system, such as a microprocessor a dedicated design hardware. It will be understood by those skilled in the art that the above-mentioned methods and systems may be implemented using computer-executable instructions and/or embedded in the control codes of a processor. For example, the control codes may be provided by a carrier medium, such as a disk, a CD, or a DVD-ROM, a programmable storage such as a read-only memory (firmware), or a data carrier such as an optical carrier or an electronic signal carrier. The system and its modules thereof of the present disclosure may be implemented by a hardware circuit such as a super large-scale integrated circuits or a gate arrays, a semiconductor such as a logic chip, a transistor, etc., or a programmable hardware device such as a field programmable gate array, a programmable logic device, etc. The system and its modules thereof may be implemented by software that can be executed by various processors, or may be implemented by a combination (e.g., firmware) of the hardware circuit and the software.

It should be noted that the above description of the candidate item display, determination systems, and modules is merely provided for the purposes of illustration, and not intended to limit the scope of the present disclosure. It will be understood that for those skilled in the art, after understanding the principle of the system, it is possible to arbitrarily combine various modules, or form subsystems to connect with other modules without departing from this principle. For example, in some embodiments, for example, the obtaining module 410, the determination module 420, and the imaging module 430 disclosed in FIG. 6 may be different modules in a system, or one module implementing functions of the two or more modules mentioned above. For example, the obtaining module 410 and the determination module 420 may be two modules, or one module having a function of obtaining instructions and determining parameters at the same time. As another example, each module may share a storage module. Each module may also have its own storage module. Those variations are still within the scope of the present disclosure.

Figure 7:
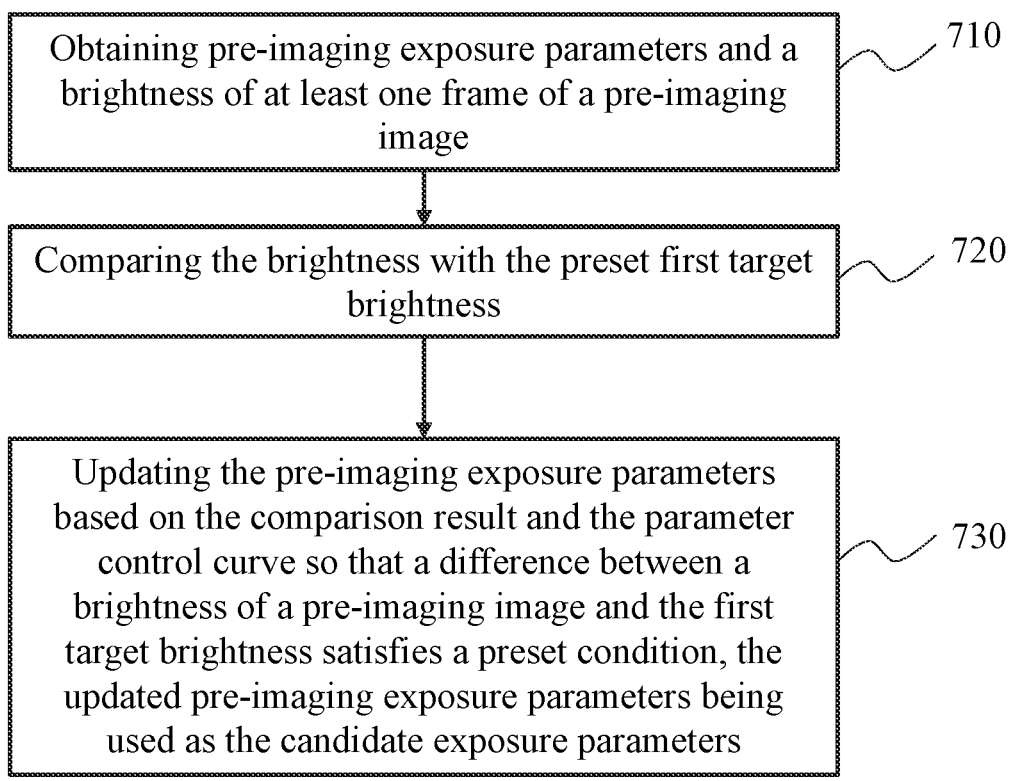
FIG. 7 is a flowchart illustrating an exemplary process for determining candidate exposure parameters according to some embodiments of the present disclosure.

FIG. 7 is a flowchart illustrating an exemplary process for obtaining candidate exposure parameters according to some embodiments of the present disclosure. In some embodiments, the process 700 may be executed by processing logic, which may include hardware (e.g., circuits, dedicated logic, programmable logic, microcodes, etc.), software (instructions that run on processing device to perform hardware simulation), or the like, or any combination thereof. One or more operations shown in the process 700 for obtaining candidate exposure parameters shown in FIG. 7 may be implemented by a system 600 for obtaining a radiographic image shown in FIG. 6 (e.g. a parameter determination unit 610 of the first determination sub-module for target exposure parameters 312 in the determination module 420). For example, the process 700 may be stored in a storage device in the form of an instruction, and called and/or executed by the system 600 for obtaining a radiographic image. As shown in FIG. 7, the process 700 may include at least one operation below.

In 710, pre-imaging exposure parameters and a brightness of at least one frame of a pre-imaging image may be obtained.

In some embodiments, the pre-imaging exposure parameters refer to the pre-set exposure parameters used in the pre-imaging process of the subject, including a tube current, a tube voltage, an irradiation duration, etc. In some embodiments, the pre-imaging exposure parameters may be stored in the processing device such as the system 600 for obtaining a radiographic image (for example, in the own storage device of the system 600 for obtaining a radiographic image), the radiographic device itself or an external storage device, or a cloud storage device. In use, the system 600 for obtaining a radiographic image may access a storage device to obtain the pre-imaging exposure parameters. In some embodiments, the pre-imaging exposure parameters may be set and input by a user (e.g., a medical staff such as a doctor a nurse). In some embodiments, a corresponding relationship between a tube voltage, a tube current, and an irradiation duration included in the pre-imaging exposure parameter may conform to the ABS curve. For example, the tube voltage, the tube current, and the irradiation duration included in the pre-imaging exposure parameters may be the tube voltage, the tube current, and the irradiation duration corresponding to a point on the ABS curve.

In some embodiments, the pre-imaging image may be an image formed by rays passing through the subject received by the imaging device after the rays are delivered to the subject according to the pre-imaging exposure parameters in the pre-imaging process. The imaging device may include a radiation detector (e.g., a gas detector, a scintillation detector, a semiconductor detector, etc.) in a radiographic device, which may convert radiation energy to be recordable. The projection data contained in the electrical signal may be processed to obtain an image. The resulting image refers to as a pre-imaging image. The brightness may be an attribute of a pre-imaging image, and the brightness may be obtained directly after the pre-imaging image is obtained.

In 720, the brightness may be compared with the preset first target brightness.

In some embodiments, the first target brightness refers to a standard brightness that sets the required requirements during the pre-imaging process. For example, the first target brightness may be a lowest brightness to ensure that the pre-imaging is sufficiently clear. In this case, when the pre-imaging image is the first target brightness, the amount of radiation delivered by the radiographic device is small, which may be less harmful to the target object (for example, a patient) as a biological body. In some embodiments, the first target brightness may be a default value of the radiographic device pre-stored in a processing device such as the system 600 for obtaining a radiographic image (e.g., in the own storage device of the system 600 for obtaining a radiographic image), in the radiographic device itself or in an external storage device, or in a cloud storage device, or input and determined by a user (for example, a doctor), which will not be limited in the present disclosure.

In some embodiments, the system 600 for obtaining a radiographic image may directly compare the value of the brightness with the value of the first target brightness. Specifically, the system 600 for obtaining a radiographic image may compare whether the value of the brightness is greater than, less than, or equal to the first target brightness, and determine the comparison result.

In 730, the pre-imaging exposure parameters may be updated based on the comparison result and the parameter control curve so that a difference between a brightness of a pre-imaging image and the first target brightness satisfies a preset condition, and the updated pre-imaging exposure parameters may be used as the candidate exposure parameters.

In some embodiments, the ABS curve may reflect a curve composed of exposure parameters (for example, a pair of tube voltage and tube current data) obtained by an object to be imaged with the same thickness under the same irradiation duration and with different brightness. On the same ABS curve, along the curve trend, the image brightness obtained by using the exposure parameters corresponding to the upper point in the curve is higher than the image brightness obtained by using the exposure parameters corresponding to the lower point. Corresponding to different thickness and different application scenarios, there may be different ABS curves. For example, there may be corresponding ABS curves corresponding to the patient's hand and head, respectively. The ABS curve may also include a universal ABS curve. The general ABS curve may be applied to most of the thickness ranges, for example, to the thickness range of most parts of the human body. Exemplary ABS curves and descriptions thereof may be found in FIG. 5 and relevant descriptions thereof.

In combination with operation 720, the comparison result may include that the brightness of the pre-imaging image is less than the first target brightness, the brightness of the pre-imaging image is equal to the first target brightness, or the brightness of the pre-imaging image is greater than the first target brightness. In some embodiments, when the brightness of the pre-imaging is less than the first target brightness, it may be stated that the amount of rays passing through the subject is smaller than the amount of rays that make the brightness of the pre-imaging image reach the first target brightness, and the amount of rays to be delivered needs to be increased. At this time, the tube current may be increased. The system 600 for obtaining a radiographic image may move upward along (for example, the direction in which the abscissa or the ordinate increases) the ABS curve, move along the curve toward (e.g., the horizontal coordinate or the ordinate of the ordinate) to determine the next point and its corresponding increased tube voltage and tube current. When the brightness of the pre-imaging image is greater than the first brightness, it may be stated that the amount of rays passing through the subject is greater than the amount of rays that make the brightness of the pre-imaging image reach the first target brightness, and the amount of delivered rays to be delivered needs to be decreased. At this time, the tube current may be decreased. The system 600 for obtaining a radiographic image may move upward along (for example, the direction in which the abscissa or the ordinate decreases) the ABS curve, move down the curve toward to determine the next point and its corresponding decreased tube voltage and tube current. The system 600 obtaining a radiographic image may control the radiographic imaging device to obtain a new pre-imaging image of the subject and its corresponding image brightness based on the updated pre-imaging exposure parameters. and compare with the first target brightness again to obtain a comparison result. The above process may be repeated until the difference between the brightness of the updated pre-imaging image and the first target brightness meets the preset condition. When the difference satisfies the preset condition, the updated pre-imaging exposure parameters may be used as the candidate exposure parameters. The difference refers to the difference between the value of the brightness of the pre-imaging image and the value of the first target brightness. The preset condition means that the absolute value of the difference between the above two brightness values is less than or equal to a brightness difference threshold. The brightness difference threshold may be a default value of the radiographic device pre-stored in a processing device such as the system 600 obtaining a radiographic image (e.g., in the own storage device of the system 600 for obtaining a radiographic image), in the radiographic device itself or in an external storage device, or in a cloud storage device, or input and determined by a user (for example, a doctor), which will not be limited in the present disclosure. It should be noted that, in the first comparison, if the difference between the value of the brightness of the pre-imaging image and the value of the first target brightness has met the preset condition, it is not necessary to update the pre-imaging exposure parameters, and directly use the pre-imaging exposure parameters for the first pre-imaging as the candidate exposure parameters.

When the brightness of the pre-imaging image is equal to the first target brightness, the system 600 for obtaining a radiographic image may directly use the pre-imaging exposure parameter as the candidate exposure parameters.

It should be noted that the above description of the process 700 is merely provided for illustration and not intended to limit the scope of the present disclosure. For those skilled in the art, various modifications and changes may be conducted to the process 700 under the teaching of the present disclosure. However, these modifications and changes are still within the scope of the present disclosure. For example, operation 730 may be divided into a plurality of operations, for example, including a judgment operation to determine whether the difference between the brightness of the pre-imaging image and the first target brightness meets a preset condition; an updating operation to update the pre-imaging exposure parameters based on the result of the judgment operation in combination with the ABS curve and return to operation 710 to perform a new iteration; and a determination operation is to use the updated pre-imaging exposure parameters as the candidate exposure parameters when the difference between the pre-imaging image brightness and the first target brightness meets a preset condition.

FIG. 8 is a flowchart illustrating an exemplary process for obtaining target exposure parameters according to some embodiments of the present disclosure. In some embodiments, the process 400 may be executed by processing logic, which may include hardware (e.g., circuits, dedicated logic, programmable logic, microcode, etc.), software (instructions that run on a processing device to perform hardware simulation), or the like, or any combination thereof. One or more operations in the process 800 for obtaining candidate exposure parameters may be implemented by the system 600 for obtaining a radiographic image shown in FIG. 6 (e.g., the parameter determination unit 610 of the first determination sub-module for target exposure parameters 312 in the determination module 420). For example, the process 800 may be stored in a storage device in the form of an instruction, and called and/or executed by the system 600 for obtaining a radiographic image. As shown in FIG. 8, the process 800 may include at least one operation below.

In 810, based on the candidate exposure parameters and the first target brightness, an equivalent thickness of the subject may be determined.

In some embodiments, the equivalent thickness refers to a calculated value representing an average thickness of a subject. The equivalent thickness may be determined based on the candidate exposure parameters, the first target brightness, and the brightness-thickness-parameter model. In some embodiments, the brightness-thickness-parameter model may be obtained after training on a plurality of brightness-thickness-parameter data pairs. The brightness-thickness-parameter data pair may be composed of an exposure parameter, a body thickness of a target to be impeded, and a corresponding brightness of the obtained imaging image. The three values in each brightness-thickness-parameter data pair may be in one-to-one correspondence and may be related to each other. The remaining one value may be determined if two of them are known. Therefore, the brightness-thickness-parameter model may at least embody a correlation between the image brightness, the object thickness, and the exposure parameters. In some embodiments, the system 600 for obtaining a radiographic image may directly input candidate exposure parameters and the first target brightness into the brightness-thickness-parameter model to obtain the equivalent thickness of the subject.

In some embodiments, the brightness-thickness-parameter model may be determined in a variety of ways, which may include function fitting, model training, or the like, or any combination thereof.

In some embodiments, the system 600 for obtaining a radiographic image (e.g., the model obtaining unit 620 in the first determination sub-module for target exposure parameters 312 in the determination module 420) may obtain the exposure parameters corresponding to the test targets of different thicknesses when the image brightness reaches a plurality of different brightness. In the present disclosure, a water model or PMMA phantom with the same degree of radiation (for example, X-rays) attenuation as the subject may be used to perform multiple radiation delivery to obtain the corresponding exposure parameters when the radiation images of the water model or phantom with different thicknesses reach different brightness. The system 600 for obtaining a radiographic image may use the data obtained above to perform function fitting, or model training to obtain the brightness-thickness-parameter model. In some embodiments, in the process of obtaining the brightness-thickness-parameter model (fitting or training), the relationship between the tube voltage and tube current included in the used exposure parameters may conform to the ABS curve. For example, the same image brightness obtained under the same thickness may correspond to a plurality of exposure parameters, such as different tube voltages, tube currents, and irradiation durations. The corresponding points of tube voltage and tube current may be on the ABS curve.

In some embodiments, the system 600 for obtaining a radiographic image (e.g., the model obtaining unit 620 in the first determination sub-module for target exposure parameters 312 in the determination module 420) may determine a plurality of fitting functions at different brightness between a plurality of test target thicknesses and their corresponding exposure parameters, and use the fitting functions as the brightness-thickness-parameter model. Exemplary data fitting methods may include linear fitting, quadratic function fitting, n-degree polynomial fitting of data, data fitting of exponential function, data fitting of multiple linear function, or the like, or any combination thereof. Merely by way of example, the data fitting process may include drawing a scatter plot of the three sets of data of brightness, thickness, and exposure parameters. An appropriate fitting function model may be determined according to the distribution of the scatter plot. The function may be fitted through the least square method. In some embodiments, the data fitting may be performed in software such as origin, matlab, SPSS, or the like. The fitting function model determined by fitting is the brightness-thickness-parameter model.

In some embodiments, the system 600 for obtaining a radiographic image (e.g., the model obtaining unit 620 in the first determination sub-module for target exposure parameters 312 in the determination module 420) may train an initial model to obtain a trained brightness-thickness-parameter model based on a plurality of test target thicknesses, exposure parameters, and the brightness of the corresponding images. The initial model shown may be a statistical model, or a machine learning model. Exemplary statistical models may include a multiple regression models, cluster analysis model, a discriminant analysis model, a principal component analysis model, a factor analysis model, a time series analysis model, or the like. Exemplary machine learning models may include a linear classifier (such as LR), a neural network model, a support vector machine (SVM), a naive bayes (NB), a K-neighbor (KNN), a decision tree (DT), an ensemble model (e.g., a RF/GDBT, etc.), etc. Merely by way of example, the system 600 for obtaining a radiographic image may select a part of the brightness, exposure parameters, and thickness data as training data, and use another part of the data as test data to train the initial model. In some embodiments, the brightness-thickness-parameter model obtained by training may be a general model, or may include a plurality of sub-models. After inputting any two values of image brightness, target thickness, and exposure parameters, the remaining one value may be obtained.

In some embodiments, the system 600 for obtaining a radiographic image (e.g., the model obtaining unit 620 in the first determination sub-module for target exposure parameters 312 in the determination module 420) may perform statistical analysis on the obtained image brightness of test targets of different thicknesses and their corresponding exposure parameters when the brightness reaches a plurality of different brightness. The obtained statistical model may be used as the brightness-thickness-parameter model.

In some embodiments, the brightness-thickness-parameter model may be a pre-determined statistical model and stored in a storage device (e.g., an internal storage of the system 600 for obtaining a radiographic image, or an external storage device connected to the system 600 for obtaining a radiographic image via a wired or wireless connection) The model obtaining unit 620 in the target exposure parameter first determination sub-model 312 in the determination module 420 may communicate with the storage device to obtain the brightness-thickness-parameter model. In some embodiments, the candidate exposure parameters and the first target brightness may be input to the determined brightness-thickness-parameter model to obtain an equivalent thickness of the subject.

In 820, based on the equivalent thickness of the subject and a second target brightness, the target exposure parameters may be determined.

In some embodiments, the second target brightness refers to the brightness required for the radiographic image obtained during the imaging process. The brightness of the radiographic image, that is, the second target brightness, may meet the requirements of diagnosis and/or determination. For example, it is necessary to meet the requirements of disease diagnosis and/or comparison and judgment of surgical progress during medical treatment. The second target brightness may be a default value of the radiographic device pre-stored in a processing device such as the system 600 for obtaining a radiographic image (e.g., in the own storage device of the system 600 for obtaining a radiographic image), in the radiographic device itself or in an external storage device, or in a cloud storage device, or input and determined by a user (for example, a doctor), which will not be limited in the present disclosure. In some embodiments, after the equivalent thickness of the subject is determined, the equivalent thickness and the second target brightness may be input into the brightness-thickness-parameter model to obtain the target exposure parameters. The target exposure parameters may include a second tube voltage, a second tube current, a second irradiation duration, or the like.

It should be noted that the above description of the process 800 is merely provided for illustration and not intended to limit the scope of the present disclosure. For those skilled in the art, various modifications and changes may be conducted to the process 800 under the teaching of the present disclosure. However, these modifications and changes are still within the scope of the present disclosure.

FIG. 9 is a schematic diagram illustrating an exemplary ABS curve according to some embodiments of the present disclosure. As shown in FIG. 9, the abscissa of the ABS curve is a tube current in mA, the ordinate is a tube voltage in kV. Three curves are shown in the figure, respectively corresponding to different applications. LD denotes a low dose mode (low dose), representing changes of the tube voltage and the tube current under a low dose. S denotes Standard, representing changes of the tube voltage and the tube current under a standard condition. HC denotes high contrast, representing changes of the tube voltage and the tube current under high contrast. The trend of the ABS curve may be reflected as the change trend of the tube voltage and the tube current to maintain the same brightness under different thicknesses. In order to maintain the brightness of the image, for different thicknesses, in the low dose mode, the trend of the ABS curve may be a large increase in tube voltage and a small increase in tube current to keep the output radiation dose low. In the standard mode, the trend of the ABS curve is that the tube current and the tube voltage rise steadily, which may be in line with the parameter change to maintain brightness in most cases. In the high contrast mode, the trend of the ABS curve is that the tube current increases rapidly, and the tube voltage rises steadily. High contrast may need to receive more radiation dosage to ensure the sharpness of the obtained radiation image. Therefore, the tube current increases rapidly. It should be noted that the above description of the ABS curve and the selection is only as exemplary, the scope of the scope of the present disclosure is not limited thereto. For example, the values corresponding to the points on the ABS curve (e.g., a tube current and a tube voltage) may be extracted to form a plurality of discrete data pairs. These data pairs may form a lookup table, which may represent changes of the tube current and the tube voltage in a form of a table. For example, parameters may be changed by looking up the table instead of moving on the curve.

Methods and systems disclosed in the embodiments of the present disclosure may be applied to a plurality of radiographic devices, such as a CT, a PET, an SPECT, a DR, a CR, a C-arm, or the like. Preferably, methods and systems disclosed in the embodiments of the present disclosure may be applied to a C-arm radiographic system. The C-arm radiographic system may include a mobile C-arm and/or a digital subtraction angiography (DSA) device.

Figure 10:
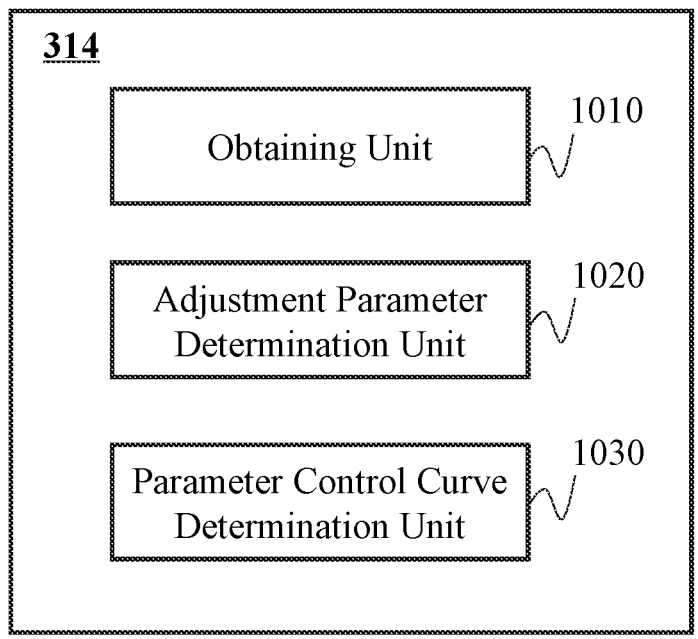
FIG. 10 is a block diagram illustrating an exemplary second determination sub-module for target exposure parameters according to some embodiments of the present disclosure.

FIG. 10 is a block diagram illustrating an exemplary second determination sub-module for target exposure parameters according to some embodiments of the present disclosure. As shown in FIG. 10, the second determination sub-module for target exposure parameters 314 may include an obtaining unit 1010, an adjustment parameter determination unit 1020, and a parameter control curve determination unit 1030.

The obtaining unit 1010 may be configured to obtain information and/or data related to adaptive control of the imaging device. Specifically, the obtaining module may be configured to obtain information reflecting a user's behavior in using an imaging device. In some embodiments, the information reflecting a user's behavior in using the imaging device may include a parameter record of the imaging device manually adjusted by a user, a user's satisfactory degree of an image output by the imaging device, a part to be imaged by a user using the imaging device, a positioning area of a region of interest in an image output by the imaging device, or the like, or any combination thereof.

The adjustment parameter determination module 1020 may be configured to determine adjustment parameters of the imaging device 110 (such as the radiation generating device 115). Specifically, the adjustment parameter determination module 1020 may determine adjustment parameters of the radiation generating device 115 in the imaging device according to the information reflecting a user's behavior in using the imaging device. In some embodiments, the adjustment parameters may include at least two of a tube voltage, a tube current, a pulse effective time, or a product of a tube current and a pulse effective time of the radiation generating device 115.

The parameter control curve determination module 1030 may be configured to determine the parameter control curve of the imaging device 110 (such as the radiation generating device 115). Specifically, the parameter control curve determination module 1030 may generate or correct the parameter control curve of the radiation generating device 115 based on the adjustment parameters. The parameter control curve may reflect a mapping relationship between at least two adjustment parameters of the radiation generating device 115. In some embodiments, the parameter control curve determination module 1030 may generate or correct a parameter control curve of the radiation generating device with respect to the part based on the adjustment parameters according to a part where a user uses the imaging device to perform imaging. In some embodiments, the parameter control curve determination module 1030 may generate or correct a parameter control curve when the radiation generating device 110 is imaged according to the positioning area based on the adjustment parameters according to a positioning area of a region of interest in an image output by the imaging device. In some embodiments, the parameter control curve determination module 1030 may determine at least a part of the parameter control curve by using an interpolation method or a regression method.

Figure 11:
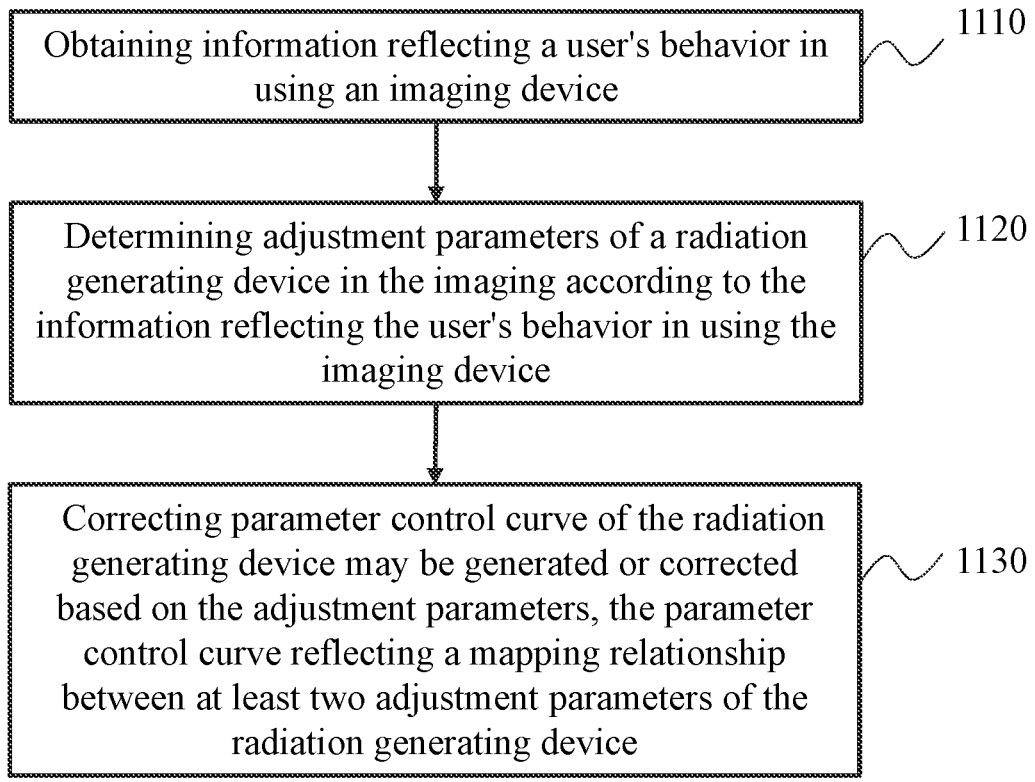
FIG. 11 is a flowchart illustrating an exemplary process for generating/updating parameter control curve according to some embodiments of the present disclosure.
Figure 12:
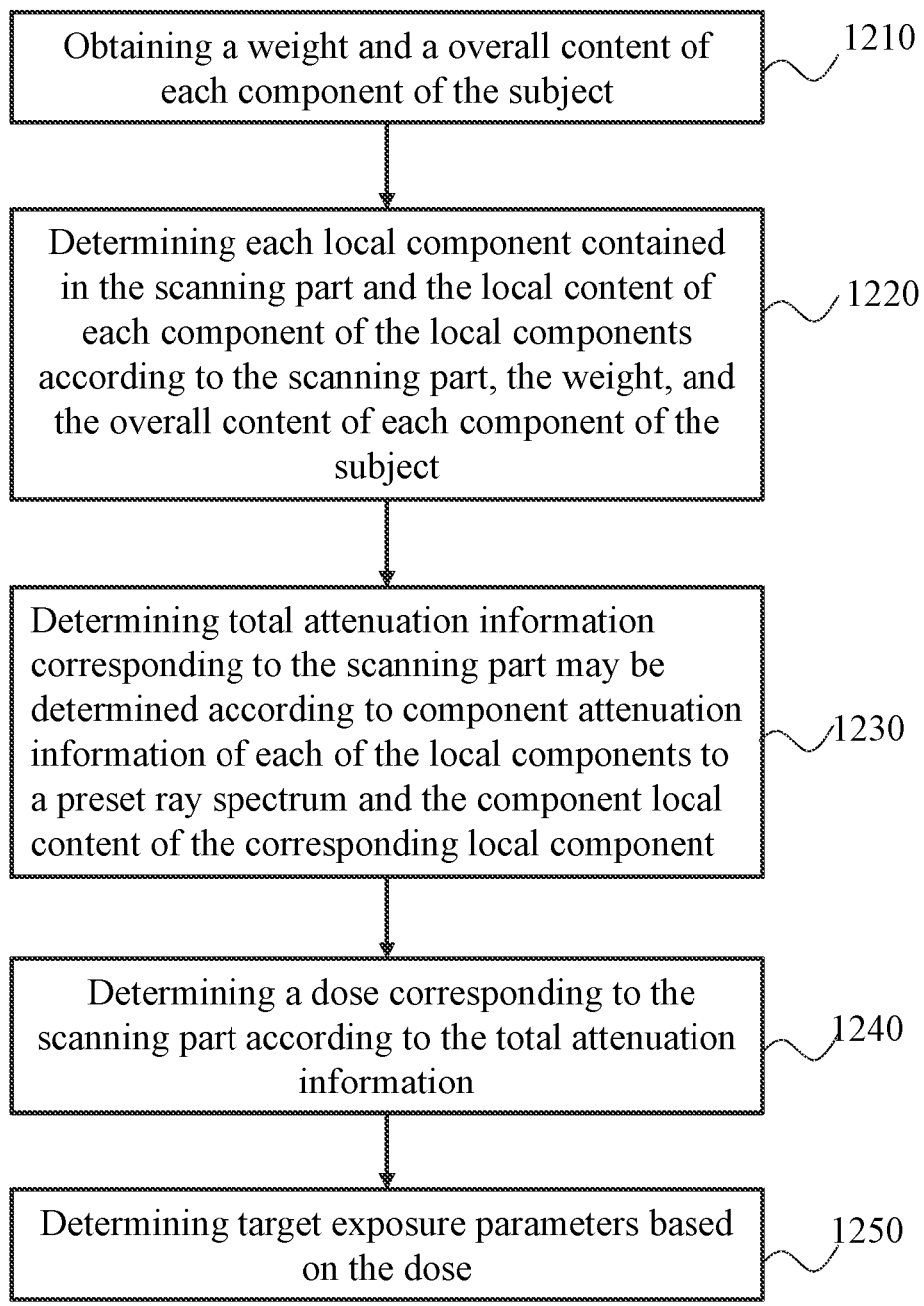
FIG. 12 is a flowchart illustrating another exemplary process for determining target exposure parameters according to some embodiments of the present disclosure.
Figure 13:
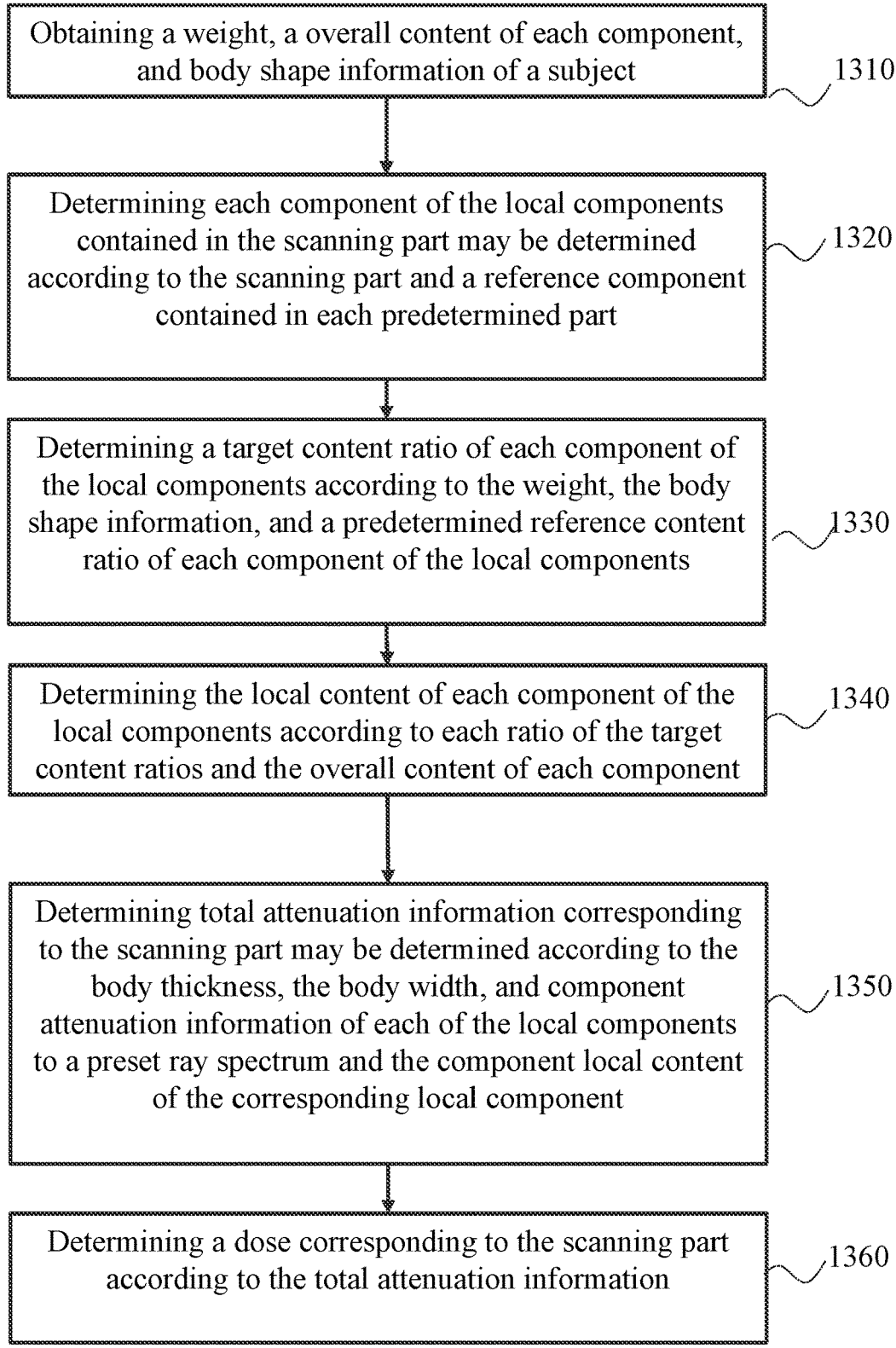
FIG. 13 is a flowchart illustrating for an exemplary process for determining a dose according to some embodiments of the present disclosure.
Figure 14:
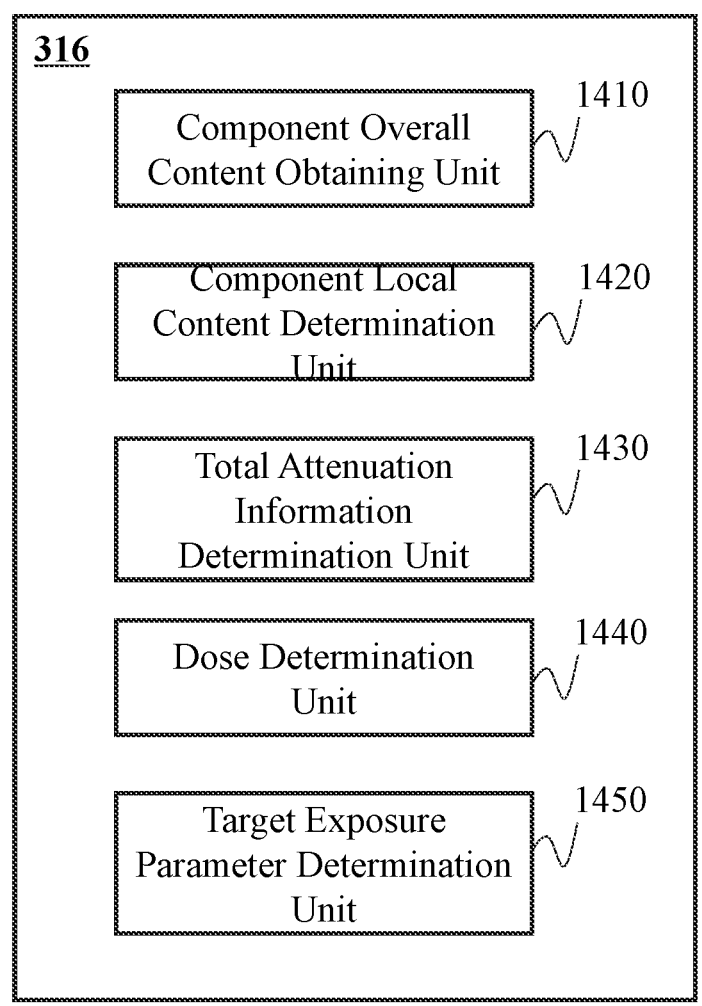
FIG. 14 is a block diagram illustrating an exemplary third determination sub-module for target exposure parameters according to some embodiments of the present disclosure.

FIG. 11 is a flowchart illustrating an exemplary process for adaptively controlling an imaging device according to some embodiments of the present disclosure. Specifically, a method 1100 for adaptively controlling an imaging device may be performed by the processing device 140. For example, the method 1100 for adaptively controlling an imaging device may be stored in a storage device (e.g., a storage device 150, a storage 220) in the form of a program or an instruction. When the imaging system 100 (such as the processing device 140) executes the program or the instruction, the method 1100 for adaptively controlling an imaging device may be implemented. In some embodiments, the process 1100 may be performed by the second determination sub-module for target exposure parameters 314. As shown in FIG. 11, the method 1100 for adaptively controlling the imaging device may include the following operations.

In 1110, information reflecting a user's behavior in using an imaging device may be obtained. Specifically, operation 1010 may be performed by the obtaining unit 1010.

In some embodiments, a user may be an operator (e.g., doctor) of the imaging device 110. In some embodiments, the same imaging device may have one or more users, and information of the behavior in using the imaging device 110 may be classified and managed on the imaging device according to different users. For example, user A may log in to the imaging device 110 using a personal account and password. After the user A uses the device to complete imaging, the imaging device 110 may correspondingly record the information of the user A's behavior in using the device in its personal account (and the corresponding storage device). In some embodiments, the information of different users' behavior in using imaging device may be the same or different.

In some embodiments, the information reflecting a user's behavior in using the imaging device may include a parameter record of the imaging device 110 manually adjusted by a user, a user's satisfactory degree of an image output by the imaging device 110, a part where a user uses the imaging device 110 to perform imaging, a positioning area of a region of interest in an image output by the imaging device 110, or the like, or any combination thereof.

In some embodiments, a parameter record of the imaging device 110 manually adjusted by a user may be a record of the user manually adjusting the parameters of the radiation generating device 115 in the imaging device 110. In some embodiments, the adjusted parameters may include at least one of a tube voltage, a tube current, or a pulse effective time of the radiation generating device 115. In some embodiments, the user may adjust one or more of the three parameters. For example, the user may adjust only the tube voltage, or only the tube current. Alternatively, the user may adjust the tube voltage and tube current, respectively. In some embodiments, the user may adjust a combination of two parameters therein. For example, the user may adjust a product of the tube current and the pulse effective time. In some embodiments, the X-ray radiation energy may be increased by increasing the tube voltage. The stronger the X-ray radiation energy is, the better the penetration effect (e.g., both muscle tissue and bones may be penetrated by X-rays), which may increase the brightness of the output image, but may reduce the contrast of the output image. In some embodiments, the X-ray radiation dose may be increased by increasing the tube current and/or the pulse effective time, which may increase the contrast of the output image to a certain extent.

In some embodiments, the user's satisfactory degree of the output image may be configured to reflect the user's preference for the output image. In some embodiments, the user's satisfactory degree of the output image may be judged according to the time the user uses the imaging device under a quality of a certain output image, a count of times the imaging device is used and whether an action indicating satisfactory degree is taken under a certain output image. In some embodiments, the quality of the output image may be reflected by the characteristic value of the output image (e.g., a signal-to-noise ratio, a resolution, a contrast, and/or an edge sharpness of an image). In some embodiments, when the imaging device 110 performs imaging by using the same parameter control curve, the quality of its output image may be considered the same. Specifically, the user using the imaging device under a quality of a certain output image may be understood as the user may use the imaging device 110 to automatically scan to obtain an output image without manually adjusting the parameters during the period (once or twice). The output image obtained by the user using the imaging device 110 to automatically scan may be a plurality of images obtained in one scanning, or a plurality of images obtained in a plurality of (continuous or cumulative) scanning. In some embodiments, the output image obtained by the user using the imaging device 110 to automatically scan may further include a plurality of output images obtained by the imaging device 110 automatically scanning (without adjusting parameters manually) for a particular one or more parts.

In some embodiments, for example, when the time (such as a continuous use time or a cumulative use time) that the user uses the imaging device 110 under a quality of a certain output image is greater than a set time threshold (such as 5 minutes, 10 minutes, half an hour, 1 hour, etc.), it may be considered that the user recognizes the output image (or this type of output image). As another example, when the count of times (such as a count of continuous use or cumulative use) that the user uses the imaging device 110 under a quality of a certain output image is greater than a preset threshold (such as 3 times, 5 times, etc.), it may be considered that the user recognizes the output image (or this type of output image). In some embodiments, the behavior that the user recognizes may include the user's saving or confirming under a certain output image. For example, a user may trigger a save control (such as saving the output image) or a confirmation control (such as confirming that the output image is feasible), etc. In some alternative embodiments, the user's satisfactory degree of the output image may also be a result of the user's scoring of the output image. In some embodiments, the scoring criterion may be a hundred-point system, a ten-point system, a percentage system, or a binary method. For example, when the score result is greater than or equal to the set score threshold (such as 90 points on the hundred-point system, 9 points on the ten-point system, 90% on the percentage system, or 1 in the binary method), it may indicate that the user recognizes the output image.

In some embodiments, the imaged part may be a tissue, an organ, and/or a body part of a subject. Specifically, the tissue may include but is not limited to muscle tissue, neuronic tissue, bone tissue, epithelial tissue, etc. The organ may include but is not limited to a heart, a liver, a lung, a stomach, a kidney, etc. The body part may include but is not limited to a head, a hand, an arm, a foot, a calf, a thigh, an abdomen, a chest, etc. In some embodiments, the imaged part may be the subject manually selected or input (such as typing input, voice input, etc.) by the user before operating the imaging device 110, or may be the subject automatically recognized by the imaging device 110 according to the output image. In some embodiments, the imaging part may also be determined by other methods well known to those skilled in the art, which will not limited in the present disclosure.

In some embodiments, the region of interest may represent the part that a user is concerned about or interested in, which may be part or all of the subject. For example, when the subject is an abdomen, the part that the user is concerned about or interested in may be a small area (such as a tumor region) in a certain organ. In some embodiments, a positioning area of a region of interest in an image output by an imaging device may be configured to represent a position of the region of interest in the output image. Specifically, the positioning area may be determined according to the distance and/or angle of the central point of the image of the region of interest relative to the center point of the output image. For example, the output image may be divided into a central region and an edge region according to the distance and/or angle relative to the central point of the output image, or divided into a central region, an upper region, a lower region, a left region, and a right region. According to the position of the central point of the image of the region of interest, the corresponding region may be determined. As another example, the central point of the image of the region of interest may be taken as the center of the circle, and the region within a certain radius may be determined as a positioning area. In some alternative embodiments, the output image may be divided into M×N blocks (M, N are positive integers), and the position of region of interest in the blocks of the output image is the positioning area. For example, in a 6×8 blocks, the image of the region of interest is located in 4 blocks of the blocks, and the 4 blocks are the positioning area.

In some embodiments, the information reflecting a user's behavior in using imaging device may be stored in a storage device (such as the storage device 150, a storage 220), and may be called by the processing device 140 (e.g., the obtaining unit 1010). In some embodiments, the information reflecting a user's behavior in using imaging device may be updated regularly or irregularly as needed.

In 1120, adjustment parameters of a radiation generating device in the imaging device may be determined according to the information reflecting a user's behavior in using the imaging device. Specifically, operation 1120 may be performed by the adjustment parameter determination module 1020.

In some embodiments, the adjustment parameters may include at least two of the tube voltage, the tube current, the pulse effective time, or the product of the tube current and the pulse effective time of the radiation generating device 115. Specifically, the adjustment parameters may be a two-dimensional or three-dimensional data points. For example, the adjustment parameters may include the tube voltage and the tube current of the radiation generating device 115. As another example, the adjustment parameters may include the tube voltage and the pulse effective time of the radiation generating device 115. As yet another example, the adjustment parameters may include the tube voltage, the tube current, and the pulse effective time of the radiation generating device 115. In some embodiments, there may be different combinations of adjustment parameters for different subject.

In some embodiments, determining adjustment parameters of the radiation generating device 115 in the imaging device according to the information reflecting a user's behavior in using the imaging device may include using at least one parameter of the parameter record of the imaging device manually adjusted by a user as an adjustment parameter of the radiation generating device in the imaging device. Specifically, when the user adjusts only one parameter, the parameters adjusted by the user and at least one parameter not adjusted by the user may be used together as the adjustment parameter of the radiation generating device 115. When the user adjusts two or three parameters, the two or three parameters adjusted by the user may be used as the adjustment parameters of the radiation generating device 115. In some embodiments, the adjustment parameters may be classified according to different subjects.

In some embodiments, determining the adjustment parameters of the radiation generating device 115 in the imaging device may include determining the parameters of the imaging device 110 corresponding to the output image as the adjustment parameters of the radiation generating device 115 in the imaging device 110 when the user's satisfactory degree of an output image of the imaging device 110 is greater than a preset threshold (for example, a user recognizes the output image). In some embodiments, the user's satisfactory degree of the output image may be judged according to the time the user uses the imaging device under a quality of a certain output image, and the count of times the imaging device is used and whether an action indicating satisfactory degree is taken under a certain output image. For example, when the time that the user uses the imaging device under a quality of a certain output image is greater than a set time threshold (such as 5 minutes, 10 minutes, half an hour, 1 hour, etc.), one or more parameters of the imaging device corresponding to the quality of the output image may be determined as the adjustment parameter of the radiation generating device 115 in the imaging device 110. As another example, when the count of times that the user uses the imaging device 110 under a quality of a certain output image is greater than a preset threshold (such as 3 times, 5 times, etc.), one or more parameters of the imaging device corresponding to the quality of the output image may be determined as the adjustment parameter of the radiation generating device 115 in the imaging device 110. As another example, when the user performs a saving or confirmation operation under the output image, the one or more parameters of the imaging device corresponding to the output image may be determined as the adjustment parameters of the radiation generating device 115 in the imaging device 110. In some alternative embodiments, when the user scores the output image, the one or more parameters of the imaging device corresponding to the output image when the score result is greater than the set score threshold may be determined as the adjustment parameter of the radiation generating device 115 in the imaging device 110.

In some embodiments, determining adjustment parameters of the radiation generating device 115 in the imaging device 110 according to the information reflecting a user's behavior in using the imaging device may further include extracting a characteristic value of the output image when the user's satisfactory degree of the image output by the imaging device 110 is greater than a preset threshold. The adjustment parameters of the radiation generating device 115 in the imaging device 110 may be determined based on the characteristic value of the output image. In some embodiments, the characteristic value of the output image may include a signal-to-noise ratio, a resolution, a contrast, an edge sharpness, or the like, or any combination thereof. In some embodiments, the correspondence between the characteristic value of the output image and the adjustment parameters of the radiation generating device 115 may be determined according to historical data. For example, the corresponding rule between the characteristic value of the output image and the adjustment parameters of the radiation generating device 115 may be determined according to historical data. As yet another example, a model (such as a machine learning model) that can be used to determine the adjustment parameters based on the characteristic values of the output image may be trained based on historical data.

In 1130, a parameter control curve of the radiation generating device may be generated or corrected based on the adjustment parameters, the parameter control curve reflecting a mapping relationship between at least two adjustment parameters of the radiation generating device. Specifically, operation 1130 may be performed by the parameter control curve determination module 1030.

In some embodiments, the adjustment parameters may include at least two of the tube voltage, the tube current, a pulse effective time, or a product of the current tube and the pulse effective time of the radiation generating device 115. In some embodiments, the parameter control curve may reflect a mapping relationship between at least two adjustment parameters of the radiation generating device 115. For example, the parameter control curve may reflect a mapping relationship between the tube voltage (kV) and the tube current (mA). As another example, the parameter control curve may reflect the mapping relationship between the tube voltage (kV) and a product (mAs) of the tube current and the pulse effective time. In some embodiments, the imaging device 110 may be preset with an initial parameter control curve. In some embodiments, the initial parameter control curve may be determined by the device vendor based on clinical experience parameters of a large number of users (such as doctors).

In some embodiments, the parameter control curve may be a segmented curve (or line segment). In some embodiments, the parameter control curve determination module 1030 may generate the entire parameter control curve of the radiation generating device based on the adjustment parameters. For example, the parameter control curve determination module 1030 may generate the parameter control curve of the radiation generating device based only on the adjustment parameters instead of the original parameters of the original parameter control curve. In some embodiments, the parameter control curve determination module 1030 may also correct the parameter control curve of the radiation generating device based on the adjustment parameters. For example, the parameter control curve determination module 1030 may correct a part of the parameter control curve based on the adjustment parameters. As another example, the parameter control curve determination module 1030 may correct the parameter control curve or a part thereof based on the adjustment parameters and the original parameters of the original parameter control curve.

In some embodiments, the parameter control curve determination module 1030 generating or correcting a parameter control curve of the radiation generating device based on the adjustment parameters may include the parameter control curve determination module 1030 may generate or correct a parameter control curve of the radiation generating device with respect to the part based on the adjustment parameters according to a part to be imaged by a user using the imaging device. During the actual imaging process, the imaging requirements for different imaging parts may be different. Therefore, different parameter control curves may be set separately for different imaging parts. When generating or correcting the parameter control curve, the parameter control curve of a certain part may be generated or corrected based on the adjustment parameter of the part.

In some embodiments, the parameter control curve determination module 1030 may generate or correct, according to a positioning area of a region of interest in an image output by the imaging device 110, a second parameter control curve when the radiation generating device 115 is imaged according to the positioning area based on the adjustment parameters. During the actual imaging process, when the parameters of the radiation generating device are determined, different positioning areas of the region of interest in the image output by the imaging device 110 may result in different effects of the output image. Therefore, different parameter control curves may be set in different positioning areas in the output image of the imaging device 110 according to the parts of interest. For example, the positioning area may be divided into two types (or more types) according to a distance between the image of the region of interest and the center of the output image. When generating or correcting the parameter control curve, the parameter control curve corresponding to the positioning area may be generated or corrected based on the adjustment parameters of the region of interest in different positioning areas.

In some embodiments, the parameter control curve determination module 1030 generating or correcting the parameter control curve of the radiation generating device 115 according to the adjustment parameters may include the parameter control curve determination module 1030 determining at least a part of the parameter control curve by using an interpolation method or a regression method. In some embodiments, the parameter control curve may be a smooth transition curve or a segmented curve. Specifically, the adjustment parameters may include a plurality of discrete points (such as points that reflect a mapping relationship between the tube voltage and the tube current). In some embodiments, the parameter control curve (or a part of the curve) may be fitted by the regression method based on the plurality of discrete points. In some embodiments, interpolation may be performed between a plurality of discrete points based on the plurality of discrete points, to obtain a parameter control curve (or a part of the curve) in the form of the segmented curve.

In some embodiments, the imaging system 100 (such as the processing device 140) may control the imaging device 110 (such as the radiation generating device 115) based on the generated or corrected parameter control curve to automatically adjust the image the brightness of the image output by the imaging device 110. Since the parameter control curve is generated or corrected according to the information of the users behavior in using the imaging device, the output image obtained based on the parameter control curve may be more in line with the users preference, reducing the user's frequency of parameter adjustment during the imaging process, improving imaging efficiency, and improving user satisfaction.

In a specific embodiment, when detecting the arm by using the imaging device, the user may manually adjust the tube voltage and the tube current of the radiation generating device in the imaging device, at this time, the processing device 140 (e.g., the obtaining unit 1010) may record the tube voltage and the tube current manually adjusted by the user. Specifically, the obtaining unit 1010 may obtain the tube voltage and the tube current manually adjusted by the user from the imaging device 110 from the imaging device 110 via the network 120. Thereafter, the data obtained by the obtaining unit 1010 from the imaging device 110 may reflect that the user does not adjust the tube voltage and the tube current in this detection (indicating that the user recognizes the manually adjusted output image). In this case, the processing device 140 (e.g., the adjustment parameter determination module 1020) may determine the manually adjusted tube voltage and the tube current as the adjustment parameters of the radiation generating device in the imaging device. Further, the processing device 140 (such as the parameter control curve determination module 1030) may use the tube voltage and the tube current manually adjusted to correct the parameter control curve of the radiation generating device (reflecting a mapping relationship between the tube voltage and the tube current). Specifically, the parameter control curve determination module 1030 may use the tube voltage and the tube current manually adjusted as a new data point, and combine the data point of the original parameter control curve to re-fit and determine the updated parameter control curve. When the user uses the imaging device to detect the arm next time, the radiation generating device may automatically adjust the brightness of the output image according to the updated parameter control curve.

It should be noted that the above description of the process 1100 and the description thereof is merely provided for illustration and not intended to limit the scope of the present disclosure. For those skilled in the art, various modifications and changes may be conducted according to the description of the present disclosure. However, those modifications and changes do not depart from the scope of the present disclosure. The adjustment parameters of the radiation generating device in the imaging device may be determined according to two or more of the information reflecting the behavior of the user in using the imaging device (that is, to meet any one of the two or more), and the parameter control curve of the radiation generating device may be generated or corrected based on the adjustment parameters. As another example, the adjustment parameters of the radiation generating device in the imaging device may be jointly determined according to the part that the user uses the imaging device to image and the positioning area of the region of interest in the output image of the imaging device, and the parameter control curve of the radiation generating device may be generated or corrected based on the adjustment parameters, the obtained parameter control curve may be applied to the situation where the specific part and the region of interest is in the specific positioning area of the imaging device.

Further description will be made below with reference to the accompanying drawings and the embodiments. It will be described that target exposure parameters may be determined based on the biological information of the subject.

Embodiment 1

In this embodiment, the method for determining a dose based on radiography may be applied to the determination of the imaging dose by using radiography. The method may be executed by a device for determining a dose based on radiation, which may be implemented by software and/or hardware, and the device may be integrated in an electronic device, such as a notebook computer, a desktop computer, a server, a network device, or the like. See FIG. 12. The method of this embodiment may include the following operations.

In 1210, a weight and an overall content of each component of the subject may be obtained.

The component overall content refers to the content of a certain component constituting a subject in the whole subject.

Specifically, since the subject has a personalized difference, if the dose is set according to a certain standard, the final imaging dose will inevitably be still not very suitable for subjects. Therefore, in order to obtain the imaging dose more suitable for the subject, the embodiment of the present disclosure needs to obtain the personalized information of the subject, that is, its weight and the overall content of each component. For example, when the subject is a human body, its weight and the overall content of water, fat, bone, and muscle that make up the human body may be obtained. The weight and the overall content of each component may be obtained by measurement or read from an external storage.

Exemplarily, obtaining an overall content of each component of the subject may include obtaining an overall content of each component of the subject based on a bio-impedance analysis.

The Bio-Impedance Analysis (BIA) may be configured to measure body fat percentage. The main principle of the BIA is to simply divide the body into conductive body fluids, muscles, etc., and non-conductive fatty tissue. During the measurement, the electrode sheet may emit a very small current through the body. If the fat ratio is high, the measured bio-impedance may be greater, and vice versa. BIA may measure the body fat percentage by using this mechanism.

Specifically, the subject may be measured by measuring instruments such as electronic scales based on the bio-impedance analysis to obtain the overall content of each component of the subject.

In 1220, each local component contained in the scanning part and the local content of each component of the local components may be determined according to the scanning part, the weight, and the overall content of each component of the subject.

The component local content refers to the content of a certain component constituting a subject in the local area of the subject.

Specifically, according to the doctor's prescription, the scanning part of the subject, such as a chest, may be known. After the scanning part is known, the components included in the scanning part may be known, that is, the local component. For example, the local components included in the chest may be bones, muscles, water, fat, etc. Thereafter, according to the weight of the subject and the overall content of each component, the local content of each local component of the scanning part may be determined, for example, the local content of bones, the local content of muscles, the local content of water, the local content of fat, etc. in the breast area may be determined.

In the specific implementation, the above-mentioned required information may be counted by using a large number of body-related big data of the subject, for example, establishing a look-up table containing information such as weight, location, local components, and component ratios, and querying and obtaining the local components of the scanning part and the component local content of each local component by using the weight of the subject as the basis of the look-up table. It is also possible to use artificial intelligence algorithms to calculate relevant information, such as constructing an artificial intelligence model of body weight, part, and component local content, so as to input the weight of the subject to calculate the local components of the scanning part and the component local content of each local component. It is also possible to construct a standard model of the human body in advance, and use the weight of the subject to correct the standard model, and read the local components of the scanning part and the component local content of each local component from the correction model.

Exemplarily, determining, according to the scanning part, the weight, and the overall content of each component of the subject, each local component contained in the scanning part, and the local content of each component of the local components may include determining, according to the scanning part and a reference component contained in each predetermined part, each component of the local components contained in the scanning part; determining, according to the weight and a predetermined reference content ratio of each component of the local components, a target content ratio of each component of the local components; and determining, according to each ratio of the target content ratios and the overall content of each component, the local content of each component of the local components.

The reference component and the reference component ratio respectively refer to the local component contained in each part of the standard model and the proportion of the local content of each component to the overall content of the corresponding component, which may be obtained through big data statistics or artificial intelligence algorithms. The target content ratio refers to the proportion of the component local content of each local component in the scanning part of the subject.

Specifically, each local component contained in the scanning part may be determined from the reference components contained in each predetermined part by using the scanning part as the search condition. Then, since the pre-determined reference content ratio of each local component is related to the standard model determined based on statistical data, it needs to be corrected according to the weight of the subject. For example, the reference content ratio of each local component may be adjusted proportionally according to the weight of the standard model and the weight of the subject to obtain the target content ratio of each local component. Finally, the product of the target content ratio of each local component and the overall content of the corresponding local component may be calculated as the component local content of the corresponding local component of the subject. The advantage of this setting is that it can more quickly determine the local components contained in the scanning part and the local content of each local component, and improve the efficiency of dose determination.

In 1230, total attenuation information corresponding to the scanning part may be determined according to component attenuation information of each of the local components to a preset ray spectrum and the component local content of the corresponding local component.

The preset ray spectrum refers to the spectrum of the radiation source used for imaging. The component attenuation information refers to the attenuation of a certain component to the irradiated ray spectrum, for example, the amount of attenuation. Exemplarily, the component attenuation information is an attenuation coefficient of the local component under the preset ray spectrum. Since the attenuation of the same composition under different ray spectrum is different, and the amount of attenuation is not easy to estimate, the attenuation coefficient may be used to measure the attenuation.

Specifically, the attenuation coefficient of each local component under the pre-set ray spectrum may be determined in advance. Then, the product of the component local content of each local component and its corresponding attenuation coefficient may be calculated, and the total attenuation information of the component corresponding to each local component may be determined. Finally, the total attenuation information of the scanning part to the preset ray spectrum may be determined according to the total attenuation information of the components of each local component.

In 1240, a dose corresponding to the scanning part may be determined according to the total attenuation information.

Specifically, after the total attenuation information of the scanning part to the preset ray spectrum is determined, the dose suitable for the scanning part may be determined according to the total attenuation information. For example, the dose corresponding to the scanning part may be determined by looking up the table according to the total attenuation information and the mapping table between the attenuation information and the set dose. Big data statistics or artificial intelligence modeling may be performed in advance based on the imaging ray spectrum, attenuation information, and the dose required for clear imaging under the attenuation information to generate a mapping table or a quantitative calculation model between the imaging ray spectrum, attenuation information and the required dose. Thereafter, the mapping table may be looked up according to the above preset ray spectrum and total attenuation information to obtain a dose corresponding to the scanning part under the preset ray spectrum. Alternatively, taking the preset ray spectrum and the total attenuation information as the input of the quantitative calculation model, after the calculation of the quantitative calculation model, the dose corresponding to the scanning part under the condition of the preset ray spectrum may be output.

In 1250, the target exposure parameters may be determined based on the dose.

Specifically, the dose may be related to the setting parameters of the radiation generating device, including a tube voltage, a tube current, an irradiation duration, or a product of a tube current and an irradiation duration. The setting parameters corresponding to the dose may be the target exposure parameter. After the dose is determined, the setting parameters of the radiation generating device may be obtained according to the mapping relationship between the dose, the body thickness of the subject, the setting parameters of the radiation generating device, and the preset brightness of the radiographic image, and then the target exposure parameters may be obtained. The above mapping relationship may be a statistical mapping table obtained based on the accumulation of a large amount of data. In another implementation, according to the trained machine learning model (for example, modeling based on the set parameters, the dose, and the target brightness of the radiation image at the dose), the dose may be input to the model to directly obtain the target exposure parameters.

By obtaining a weight and an overall content of each component of the subject; determining, according to the scanning part, the weight, and the overall content of each component of the subject, each local component contained in the scanning part, and the local content of each component of the local components; determining, according to component attenuation information of each of the local components to a preset ray spectrum and the component local content of the corresponding local component, total attenuation information corresponding to the scanning part; and determining, according to the total attenuation information, a dose corresponding to the scanning part; The technical solution of the embodiment can realize the determination of the imaging dose more suitable for the subject according to the individual information of the subject and the scanning position by obtaining the weight of the subject and the overall content of each component, improve the accuracy of imaging dose determination, reduce the damage of the subject from excessive doses of radiation, and also reduce the imaging workload of the scanning technician due to repeated adjustments.

Embodiment 2

On the basis of the first embodiment described above, "obtaining body shape information of the subject, the body shape information including a height, a body width, and a body thickness" is added in this embodiment. On this basis, it is possible to further optimize the "determining, according to the scanning part, the weight, and the overall content of each component of the subject, each local component contained in the scanning part, and the local content of each component of the local components". On the basis of the above, it is also possible to further optimize the "determining, according to component attenuation information of each of the local components to a preset ray spectrum and the component local content of the corresponding local component, total attenuation information corresponding to the scanning part". The interpretation of the same or corresponding terms in the above embodiments will not be repeated herein. See FIG. 13. The method for determining a dose based on radiography may include the following operations.

In 1310, a weight, an overall content of each component, and body shape information of a subject may be obtained.

The body shape information may include a height, a body width, and a body thickness.

Specifically, considering that the body shape information of different subjects under the same weight may be different, and different body shape information will cause the local content of the local components of the scanning part to be different, or the distribution of the local components when the local content of the same component is different, all of which may cause different attenuation of the preset ray spectrum by the local components, resulting in different doses. Therefore, in this embodiment, in addition to the weight of the subject and the overall content of each component, the body shape information such as a height, a body width, and a body thickness of the subject may be obtained.

In 1320, each component of the local components contained in the scanning part may be determined according to the scanning part and a reference component contained in each predetermined part.

In 1330, a target content ratio of each component of the local components may be determined according to the weight, the body shape information, and a predetermined reference content ratio of each component of the local components.

Specifically, considering that different body shape information under the same weight may cause the local content of the local components of the scanning part to be different, therefore, the weight and body shape information of the subject may be used to correct the reference content ratio of each local component in the scanning part, and obtain the target content ratio of each local component in the scanning part.

In 1340, the local content of each component of the local components may be determined according to each ratio of the target content ratios and the overall content of each component.

In 1350, total attenuation information corresponding to the scanning part may be determined according to the body thickness, the body width, and component attenuation information of each of the local components to a preset ray spectrum and the component local content of the corresponding local component.

Specifically, in the case of the same local ingredients and the same local content of the local ingredients, different body thickness and body width may cause the local component to have a different distribution in the scanning position. Different local component distributions may cause the local component to have a different attenuation of the preset ray spectrum. For example, when the local content of the same component is different, and the corresponding body thickness and/or body width are different, the density and thickness of the local component may be different at the scanning position, and the total attenuation information of the corresponding component may be different. Therefore, in this embodiment, when determining the total attenuation information of the component corresponding to each local component in the scan position, the body thickness and body width in the body shape information may be also considered. During specific implementation, for example, the mapping relationship between body thickness, body width, and component attenuation information of different components under different imaging ray spectra may be established in advance, then, according to the preset ray spectrum, the body thickness and width of the subject, and the constructed mapping relationship, the corrected component attenuation information of each local component corresponding to the scanning part of the subject may be determined. Finally, the total attenuation information of the scanning part may be determined by using the corrected component attenuation information and component local content of each local component.

In 1360, a dose corresponding to the scanning part may be determined according to the total attenuation information.

The technical solution of this embodiment can more accurately restore the whole model of the subject by introducing the body shape information of the subject in the process of determining the target content ratio of each local component, improving the accuracy of determining the target content ratio, and further improving the accuracy of determining the subsequent dose to a certain extent. By introducing the body thickness and the body width of the subject during determining the total attenuation information corresponding to the scanning part, the determination accuracy of the total attenuation information can be improved, thereby further improving the determination accuracy of the dose.

A device for determining a dose based on radiography is provided below according to an embodiment of the present disclosure, which belongs to the same inventive concept as the method for determining a dose based on radiography of the foregoing embodiments. Details not described in detail in the embodiment of the device for determining a dose based on radiography may be found in the above embodiment of the method for determining a dose based on radiography.

Embodiment 3

This embodiment provides a block diagram illustrating an exemplary third determination sub-module for target exposure parameters 316 based on radiography. See FIG. 14. The third determination sub-module for target exposure parameters 316 may specifically include a component overall content obtaining unit 1410, a component local content determination unit 1420, a total attenuation information determination unit 1430, and a target exposure parameter determination unit 1450.

The component overall content obtaining unit 1410 may be configured to obtain a weight and an overall content of each component of the subject.

The component local content determination unit 1420 may be configured to determining each local component contained in the scanning part, and the local content of each component of the local components according to the scanning part, the weight, and the overall content of each component of the subject.

The total attenuation information determination unit 1430 may be configured to determining total attenuation information corresponding to the scanning part according to component attenuation information of each of the local components to a preset ray spectrum and the component local content of the corresponding local component.

The dose determination unit 1440 may be configured to determine a dose corresponding to the scanning part according to the total attenuation information.

The target exposure parameter determination unit 1450 may be configured to determine the target exposure parameters based on the dose.

Alternatively, the component overall content obtaining unit 1410 may be specifically configured to:
  obtain an overall content of each component of the subject based on the Bio-impedance analysis.

Alternatively, the component local content determination unit 1420 may be specifically configured to:
  determine, according to the scanning part and a reference component contained in each predetermined part, each component of the local components contained in the scanning part;
  determine, according to the weight and a predetermined reference content ratio of each component of the local components, a target content ratio of each component of the local components; and
  determine, according to each ratio of the target content ratios and the overall content of each component, the local content of each component of the local components.

Alternatively, on the basis of the above device, the sub-module may further include a body shape information obtaining unit configured to:
  obtain body shape information of the subject. The body shape information may include a height, a body width, and a body thickness.

Further, the component local content determination unit 1420 may be also specifically configured to:
  determine, according to the scanning part and a reference component contained in each predetermined part, each component of the local components contained in the scanning part;
  determine, according to the weight, the body shape information, and a predetermined reference content ratio of each component of the local components, a target content ratio of each component of the local components; and
  determine, according to each ratio of the target content ratios and the overall content of each component, the local content of each component of the local components.

Further, the total attenuation information determination unit 1430 may be specifically configured to:
  determine, according to the body thickness, the body width, and component attenuation information of each of the local components to a preset ray spectrum and the component local content of the corresponding local component, total attenuation information corresponding to the scanning part.

Alternatively, the component attenuation information is the attenuation coefficient of the local component under a preset ray spectrum.

Through a device for determining a dose based on radiography in Embodiment 3 of the present disclosure, it is possible to determine an imaging dose that is more suitable for the subject according to the individual information of the subject and the scanning part, improving the accuracy of imaging dose, reducing the damage to the subject from excessive doses of radiation, and reducing the imaging workload of scanning technicians due to repeated adjustments.

The device for determining a dose based on radiography provided by the embodiment of the present disclosure can execute the method for determining a dose based on radiography provided by any embodiment of the present disclosure, and has corresponding functional modules and beneficial effects for the execution method.

It is worth noting that the units and modules included in the above embodiment of the device for determining a dose based on radiography are only divided according to functional logic, but are not limited to the above division, as long as the corresponding functions can be achieved. In addition, the specific names of the functional units are only used to facilitate distinguishing from each other, and are not used to limit the protection scope of the present disclosure.

Embodiment 4

Figure 15:
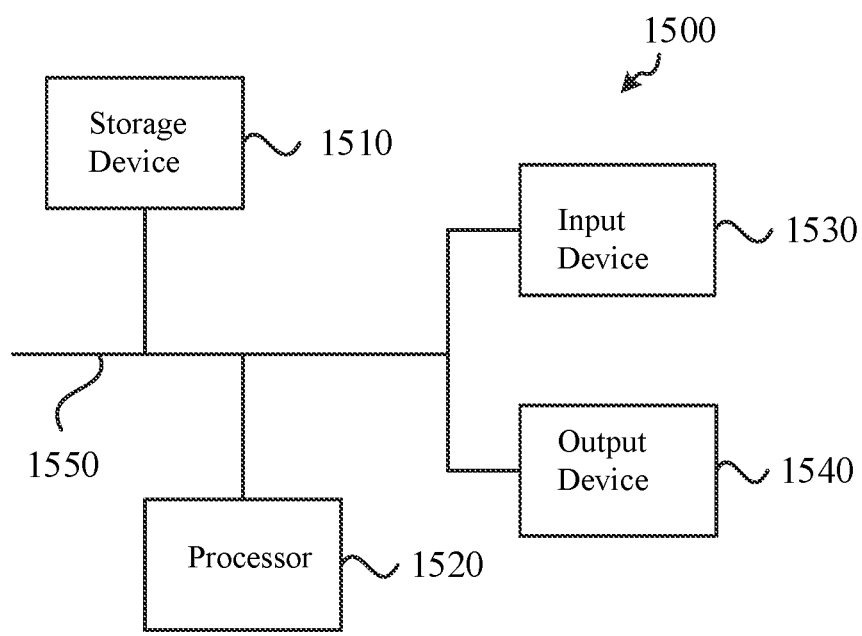
FIG. 15 is a schematic diagram illustrating exemplary hardware and/or software components of an exemplary computing device according to some embodiments of the present disclosure.

See FIG. 15. This embodiment provides an electronic device 1500, including one or more processors 1520 and a storage device 1510. The storage device 1510 may be configured to store one or more programs. When the one or more programs are executed by the one or more processors 1520, the one or more processors 1520 may implement a method for determining a dose based on radiography according to some embodiments of the present disclosure, including:
  obtaining a weight and an overall content of each component of the subject;
  determining, according to the scanning part, the weight, and the overall content of each component of the subject, each local component contained in the scanning part, and the local content of each component of the local components;
  determining, according to component attenuation information of each of the local components to a preset ray spectrum and the component local content of the corresponding local component, total attenuation information corresponding to the scanning part;
  determining, according to the total attenuation information, a dose corresponding to the scanning part; and
  determining, based on the dose, the target exposure parameters.

Of course, those skilled in the art will appreciate that the processor 1520 may also implement a technical solution of the method for determining the target exposure parameter based on radiography according to any embodiment of the present disclosure.

The electronic device 1500 shown in FIG. 15 is merely an example and should not be restricted to the functions of the embodiments of the present disclosure.

As shown in FIG. 15, the electronic device 1500 may include a processor 1520, a storage device 1510, an input device 1530, and an output device 1540. The count of the processor(s) 1520 in the electronic device may be one or more. One processor 1520 is taken as an example in FIG. 15. The processor 1520, the storage device 1510, the input device 1530, and the output device 1540 in the electronic device may be connected through a bus or other methods. In FIG. 15, the connection through the bus 1550 is taken as an example.

The storage device 1510, as a computer-readable storage medium, may be configured to store software programs, computer-executable programs, and modules, such as program instructions/modules corresponding to the method for determining a dose based on radiography in the embodiment of the present disclosure. (For example, the component overall content obtaining unit, the component local content determination unit, the total attenuation information determination unit, the dose determination unit in the device for determining a dose based on radiography).

The storage device 1510 may mainly include a program storage area and a data storage area, wherein the program storage area may store an operating system, an application program required by at least one function. The data storage area may store data created according to the use of the terminal, or the like. Further, the storage device 1510 may include a high-speed random access storage, and may further include a non-volatile storage, such as at least magnetic disk storage device, a flash memory device, or other non-volatile solid-state storage devices. In some examples, the storage device 1510 may further include a storage provided remotely with respect to the processor 1520, and these remote storages may be connected to the electronic device via a network. Examples of the above network may include but are not limited to, the Internet, an enterprise internal network, a local area network, a mobile communication network, or any combination thereof.

The input device 1530 may be configured to receive the input digital or character information, and generate key signal input related to user settings and functional control of the electronic device. The output device 1540 may include a display device such as a display screen.

Embodiment 5

This embodiment provides a storage medium containing computer-executable instructions. When executed by a computer processor, the computer-executable instruction may be configured to perform a method for determining target exposure parameters based on radiography, including:

obtaining a weight and an overall content of each component of the subject;

determining, according to the scanning part, the weight, and the overall content of each component of the subject, each local component contained in the scanning part, and the local content of each component of the local components;

determining, according to component attenuation information of each of the local components to a preset ray spectrum and the component local content of the corresponding local component, total attenuation information corresponding to the scanning part;

determining, according to the total attenuation information, a dose corresponding to the scanning part; and determining, based on the dose, the target exposure parameters.

Of course, this embodiment of the present disclosure provides a storage medium containing computer-executable instructions. The computer-executable instructions are not limited to the above method operations, and can also perform related operations in the method for determining a dose based on radiography provided by any embodiment of the present disclosure.

Through the above description of the implementation, those skilled in the art can clearly understand that the present disclosure can be implemented by software and necessary general-purpose hardware, and of course can also be implemented by hardware, but the former is a better implementation in many cases. Based on this understanding, the technical solution of the present disclosure may be embodied in the form of a software product in essence or a part that contributes to the existing technology. The computer software product may be stored in a computer-readable storage medium, such as a computer floppy disk, a read-only memory (ROM), a random access memory (RAM), a flash memory (FLASH), a hard disk or an optical disk and include a number of instructions to direct an electronic device (such as a personal computer, a server, or a network device, etc.) to execute the method for determining a dose based on radiography provided by each embodiment of the present disclosure.

It should be noted that the above is only preferred embodiments and the technical principles applied in the present disclosure. Those skilled in the art will understand that the present disclosure is not limited to the specific embodiments described herein, and various obvious changes, readjustments, and substitutions may be made to those skilled in the art without departing from the protection scope of the present disclosure. Therefore, although the present disclosure has been described in more detail through the above embodiments, the present disclosure is not limited to the above embodiments, and may also include more other equivalent embodiments without departing from the concept of the present disclosure, and the scope of the present disclosure is determined by the scope of the appended claims.

The beneficial effects of the embodiments of the present disclosure may include but are not limited to:

(1) Combining the pre-imaging process (fluoroscopy process) and the imaging process (single frame acquisition) into one operation can ensure the accuracy of the exposure parameters used in the imaging process, reduce the count of imaging times (for example, the count of exposures), and improve the user experience.

(2) Two operations are completed with one command transmission, which can reduce the radiation time and is beneficial to the health of the patient.

(3) Different parameter control curves can be determined according to the different needs of different users, thereby reducing the frequency of user adjustments, improving imaging efficiency, and improving user satisfaction.

(4) The information of the users behavior in using the imaging device can be automatically collected, and the parameter control curve can be automatically generated and corrected without the users additional operation.

(5) The user behavior information collected is diverse, and user needs can be accurately determined.

(6) The imaging dose that is more suitable for the subject can be determined according to the individual information of the subject and the scanning part, improving the accuracy of imaging dose determination, reducing the damage to the subject from excessive doses of radiation, and reducing the imaging workload of scanning technicians due to repeated adjustments.

It should be noted that different embodiments may have different beneficial effects. In different embodiments, the possible beneficial effects may include any combination of one or more of the above, or any other possible beneficial effects that may be obtained.

Some embodiments of the present disclosure and/or some other embodiments are described above. Different modifications may also be made in the present disclosure according to above content. The subject matter disclosed in the present disclosure can be implemented in different forms and embodiments, and the present disclosure can be applied to a large number of applications. All applications, modifications and changes claimed in the following claims belong to the scope of the present disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various parts of this specification are not necessarily all referring to the same embodiment. In addition, some features, structures, or features in the present disclosure of one or more embodiments may be appropriately combined.

Those skilled in the art will appreciate that there may be a variety of variations and improvements in the contents disclosed herein. For example, the different system components described above are implemented by hardware devices, but may also be implemented only by software solutions. For example, a system may be installed on an existing server. Further, the location information disclosed herein may be provided through a firmware, a combination of firmware/software, a combination of firmware/hardware, or a combination of hardware/firmware/software.

All software or some of them may sometimes communicate via the network, such as the Internet or other communication networks. Such communication can load software from one computer device or processor to another computer device or processor. For example, a hardware platform loaded from a management server or host computer of a radiotherapy system to a computer environment, or other computer environment for realizing the system, or a system with similar functions related to providing information required to determine the target structure parameters of a wheelchair. Therefore, another medium that can transmit software elements can also be used as a physical connection between local devices. For example, light waves, electric waves, electromagnetic waves, etc., spread through cables, optical cables or air. The physical media used for carrier waves, such as cables, wireless connections, or optical cables, can also be considered as media carrying software. Unless the usage herein limits the tangible "storage" medium, other terms that refer to the computer or machine "readable medium" all refer to the medium that participates in the process of executing any instructions by the processor.

Computer program code for carrying out operations for aspects of the present disclosure may be written in any combination of one or more programming languages, including an object oriented programming language such as Java, Scala, Smalltalk, Eiffel, JADE, Emerald, C++, C#, VB.NET, Python or the like, conventional procedural programming languages, such as the "C" programming language, Visual Basic, Fortran 2003, Perl, COBOL 2002, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, e.g., an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various embodiments. However, this disclosure does not mean that the present disclosure object requires more features than the features mentioned in the claims. Rather, claimed subject matter may lie in less than all features of a single foregoing disclosed embodiment.

In some embodiments, the numbers expressing quantities, properties, and so forth, used to describe and claim certain embodiments of the application are to be understood as being modified in some instances by the term "about," "approximate," or "substantially." For example, "about," "approximate," or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the present disclosure are approximations, the numerical values set forth in the specific examples are reported as precisely as practicable.

Each of the patents, patent applications, publications of patent applications, and other material, such as articles, books, specifications, publications, documents, and/or the like, referenced herein is hereby incorporated herein by this reference in its entirety for all purposes, excepting any prosecution file history associated with same, any of same that is inconsistent with or in conflict with the present document, or any of same that may have a limiting effect as to the broadest scope of the claims now or later associated with the present document. It should be noted that if the description, definition, and/or terms used in the appended application of the present disclosure is inconsistent or conflicting with the content described in the present disclosure, the use of the description, definition and/or terms of the present disclosure shall prevail.

At last, it should be understood that the embodiments described in the present disclosure are merely illustrative of the principles of the embodiments of the present disclosure. Other modifications that may be employed may be within the scope of the present disclosure. Thus, by way of example, but not of limitation, alternative configurations of the embodiments of the present disclosure may be utilized in accordance with the teachings herein. Accordingly, embodiments of the present disclosure are not limited to that precisely as shown and described.

What is claimed is:

1. A method for obtaining a radiographic image, comprising:
    obtaining a control instruction for controlling an imaging device to image a subject;
    based on the control instruction,
        determining target exposure parameters based on at least a parameter control curve or biological information of the subject, wherein the parameter control curve includes a preset first parameter control curve or a second parameter control curve, and the biological information includes at least a weight and an overall content of each component of the subject, the second parameter control curve being determined based on operation data of the imaging device; and
        imaging, based on the target exposure parameters, the subject to obtain the radiographic image.

2. The method of claim 1, wherein the target exposure parameters are determined based on the parameter control curve, and imaging, based on the target exposure parameters, the subject to obtain the radiographic image comprises:
    pre-imaging the subject based on the control instruction,
    obtaining, based on a pre-imaging result and the parameter control curve, candidate exposure parameters;
    generating, based on the candidate exposure parameters, the target exposure parameters; and
    imaging, based on the target exposure parameters, the subject again to obtain the radiographic image.

3. The method of claim 1, wherein the second parameter control curve is determined by:
    obtaining operation data of the imaging device, the operation data at least including information reflecting a user's behavior in using the imaging device;
    determining, according to the information reflecting the user's behavior in using the imaging device, adjustment parameters of a radiation generating device in the imaging device; and
    generating or correcting, based on the adjustment parameters, a second parameter control curve of the radiation generating device, the second parameter control curve reflecting a mapping relationship between at least two adjustment parameters of the radiation generating device, and the at least two adjustment parameters including at least two of a tube voltage, a tube current, an irradiation duration, or a product of a tube current and an irradiation duration.

4. The method of claim 1, wherein the determining, based on biological information of the subject, the target exposure parameters comprises:
    obtaining a weight and an overall content of each component of the subject;
    determining each local component contained in the scanning part and the local component content of each component of the local components according to a scanning part, the weight, and the overall content of each component of the subject;
    determining, according to component attenuation information of each of the local components to a preset ray spectrum and the component local content of the corresponding local component, total attenuation information corresponding to the scanning part;
    determining, according to the total attenuation information, a dose corresponding to the scanning part; and
    determining, based on the dose, the target exposure parameters.

5. A system for obtaining a radiographic image, comprising at least one processor and at least one storage; wherein the storage is configured to store instructions, and when executing the instructions, the processor is configured to direct the system to perform at least one operation of operations including:
    obtaining a control instruction for controlling an imaging device to image a subject;
    based on the control instruction,
        determining target exposure parameters based on at least a parameter control curve or biological information of the subject, wherein the parameter control curve includes a preset first parameter control curve or a second parameter control curve, and the biological information includes at least a weight and an overall content of each component of the subject, the second parameter control curve being determined based on operation data of the imaging device; and
        imaging, based on the target exposure parameters, the subject to obtain the radiographic image.

6. The system of claim 5, wherein the target exposure parameters are determined based on the parameter control curve, and to image the subject based on the target exposure parameters to obtain the radiographic image, the system performs operations including:
    based on the control instruction,
        pre-imaging the subject, and obtaining, based on a pre-imaging result and the parameter control curve, candidate exposure parameters;
        generating, based on the candidate exposure parameters, the target exposure parameters; and
        imaging the subject again to obtain, based on the target exposure parameters, the radiographic image.

7. The system of claim 6, wherein to obtain candidate exposure parameters, the system performs operations including:
    obtaining pre-imaging exposure parameters, and a brightness of at least one frame of a pre-imaging image;

comparing the brightness to a preset first target brightness; and updating, based on the comparison result and the parameter control curve, the pre-imaging exposure parameters so that a difference between a brightness of a pre-imaging image and the first target brightness satisfies a preset condition, and using the updated pre-imaging exposure parameters as the candidate exposure parameters.

8. The system of claim 7, wherein to generate, based on the candidate exposure parameters, the target exposure parameters, the system performs operations including:

determining, based on the candidate exposure parameters and the first target brightness, an equivalent thickness of the subject; and determining, based on the equivalent thickness of the subject and a second target brightness, the target exposure parameters.

9. The system of claim 8, wherein to determine an equivalent thickness of the subject, the system performs operations including:

determining, based on the candidate exposure parameters, the first target brightness, and a brightness-thickness-parameter model, the equivalent thickness of the subject; the brightness-thickness-parameter model including at least a correlation between an image brightness, a subject thickness, and exposure parameters.

10. The system of claim 9 wherein the exposure parameters in the brightness-thickness-parameter model include a tube voltage and a tube current; and a relationship between the tube voltage and the tube current obeys the parameter control curve.

11. The system of claim 5, wherein to determine the second parameter control curve, the system performs operations including:

obtaining operation data of the imaging device, the operation data at least including information reflecting a user's behavior in using the imaging device;

determining, according to the information reflecting a user's behavior in using the imaging device, adjustment parameters of a radiation generating device in the imaging device; and generating or correcting, based on the adjustment parameters, a second parameter control curve of the radiation generating device, the second parameter control curve reflecting a mapping relationship between at least two adjustment parameters of the radiation generating device, and the at least two adjustment parameters including at least two of a tube voltage, a tube current, an irradiation duration, or a product of a tube current and an irradiation duration.

12. The system of claim 11, wherein the information reflecting a user's behavior in using the imaging device comprises at least one of a parameter record of the imaging device manually adjusted by a user, a user's satisfactory degree of an image output by the imaging device, a part to be imaged by a user using the imaging device, or a positioning area of a region of interest in an image output by the imaging device.

13. The system of claim 11, wherein to determine adjustment parameters of a radiation generating device in the imaging device according to the information reflecting a user's behavior in using the imaging device, the system performs operations including:

using at least one parameter of a parameter record of the imaging device that is manually adjusted by a user as an adjustment parameter of the radiation generating device in the imaging device; or determining parameters of an imaging device corresponding to an output image as adjustment parameters of the radiation generating device in the imaging device when a user's satisfactory degree of the image output by the imaging device is greater than a preset threshold; or extracting a characteristic value of an output image when a user's satisfactory degree of the image output by the imaging device is greater than a preset threshold; and determining, based on the characteristic value of the output image, adjustment parameters of the radiation generating device in the imaging device.

14. The system of claim 11, wherein to generate or correct a second parameter control curve of the radiation generating device based on the adjustment parameters, the system performs operations including:

generating or correcting, according to a part to be imaged by a user using the imaging device, a second parameter control curve of the radiation generating device with respect to the part based on the adjustment parameters; or generating or correcting, according to a positioning area of a region of interest in an image output by the imaging device, a second parameter control curve when the radiation generating device irradiates according to the positioning area based on the adjustment parameters; or determining, according to the adjustment parameters, at least a part of the second parameter control curve by using an interpolation method or a regression method.

15. The system of claim 5 wherein to determine the target exposure parameters based on biological information of the subject, the system performs operations including:

obtaining a weight and an overall content of each component of the subject;

determining each local component contained in the scanning part and the local content of each component of the local components according to the scanning part, the weight, and the overall content of each component of the subject;

determining, according to component attenuation information of each of the local components to a preset ray spectrum and the component local content of the corresponding local component, total attenuation information corresponding to the scanning part;

determining, according to the total attenuation information, a dose corresponding to the scanning part; and determining, based on the dose, the target exposure parameters.

16. The system of claim 15, wherein to determine each local component contained in the scanning part, and the local content of each component of the local components according to the scanning part, the weight, and the overall content of each component of the subject, the system performs operations including:

determining, according to the scanning part and a reference component contained in each predetermined part, each component of the local components contained in the scanning part;

determining, according to the weight and a predetermined reference content ratio of each component of the local components, a target content ratio of each component of the local components; and determining, according to each ratio of the target content ratios and the overall content of each component, the local content of each component of the local components.

17. The system of claim 15, further performing operations including:
obtaining body shape information of the subject, the body shape information including a height, a body width, and a body thickness.

18. The system of claim 17, wherein to determine each local component contained in the scanning part, and the local content of each component of the local components according to the scanning part, the weight, and the overall content of each component of the subject, the system performs operations including:
determining, according to the scanning part and a reference component contained in each predetermined part, each component of the local components contained in the scanning part;
determining, according to the weight, the body shape information, and a predetermined reference content ratio of each component of the local components, a target content ratio of each component of the local components; and
determining, according to each ratio of the target content ratios and the overall content of each component, the local content of each component of the local components.

19. The system of claim 17, wherein to determine total attenuation information corresponding to the scanning part according to component attenuation information of each of the local components to a preset ray spectrum and the component local content of the corresponding local component, the system performs operations including:
determining, according to the body thickness, the body width, and component attenuation information of each of the local components to a preset ray spectrum and the component local content of the corresponding local component, total attenuation information corresponding to the scanning part.

20. The system of claim 17, wherein to determine the target exposure parameters based on the dose, the system performs operations including:
determining, based on the dose, the target exposure parameters by using a mapping model, the mapping model reflecting a mapping relationship between a dose, exposure parameters, and a body thickness.

* * * * *